United States Patent
Sauer et al.

(10) Patent No.: US 11,883,016 B2
(45) Date of Patent: Jan. 30, 2024

(54) SECURING BIDIRECTIONAL SUTURE LOOPS USING COAXIAL FASTENERS

(71) Applicant: LSI Solutions, Inc., Victor, NY (US)

(72) Inventors: Jude S. Sauer, Pittsford, NY (US); Angelo Martellaro, Shortsville, NY (US)

(73) Assignee: LSI Solutions, Inc., Victor, NY (US)

( * ) Notice: Subject to any disclaimer, the term of this patent is extended or adjusted under 35 U.S.C. 154(b) by 703 days.

(21) Appl. No.: 14/763,970

(22) PCT Filed: Sep. 25, 2013

(86) PCT No.: PCT/US2013/061522
§ 371 (c)(1),
(2) Date: Sep. 17, 2019

(87) PCT Pub. No.: WO2014/143161
PCT Pub. Date: Sep. 18, 2014

(65) Prior Publication Data
US 2021/0315564 A1    Oct. 14, 2021

Related U.S. Application Data

(63) Continuation of application No. 13/840,481, filed on Mar. 15, 2013, now abandoned.

(51) Int. Cl.
*A61B 17/04*    (2006.01)
*A61B 17/00*    (2006.01)
*A61F 2/24*    (2006.01)

(52) U.S. Cl.
CPC ...... *A61B 17/0469* (2013.01); *A61B 17/0485* (2013.01); *A61B 17/0487* (2013.01);
(Continued)

(58) Field of Classification Search
CPC ............ A61B 17/0469; A61B 17/0487; A61B 17/0467; A61B 2017/0488;
(Continued)

(56) References Cited

U.S. PATENT DOCUMENTS 5,520,702 A * 5/1996 Sauer ................. A61B 17/0469
606/139
5,643,289 A    7/1997 Sauer
(Continued)

FOREIGN PATENT DOCUMENTS

WO    WO2006130693    12/2006
WO    WO2012005671    1/2012

OTHER PUBLICATIONS

Jan. 20, 2016 Foreign Search Report; European Search Report for Patent No. EP 2967536.
(Continued)

*Primary Examiner* — Jing Rui Ou
(74) *Attorney, Agent, or Firm* — Michael E. Coyne

(57) ABSTRACT

A method and apparatus for securing separate loops of suture with a coaxial mechanical fastener. Separate loops of suture extend from opposite ends of the mechanical fastener. A wire snare facilitates pulling the suture through the fastener. A suturing instrument provides for the infusion of pressurized physiologic solutions into the left ventricle so that the proper replacement suture length can be demonstrated real time prior to crimping the fastener. The instrument incorporates a slotted release site so that the fastener and suture can be released from the device tip once the fastener is secured. A method of securing suture coming from cardiac valve leaflets and or other structures like papillary muscles permits a more atraumatic orientation of the fastener coaxial with the suture strands.

8 Claims, 33 Drawing Sheets

(52) U.S. Cl.
CPC . *A61B 17/0467* (2013.01); *A61B 2017/00243* (2013.01); *A61B 2017/00358* (2013.01); *A61B 2017/0488* (2013.01); *A61F 2/2457* (2013.01)

(58) Field of Classification Search
CPC ...... A61B 17/0485; A61B 2017/00243; A61B 2017/00358; A61F 2/2457
See application file for complete search history.

(56) References Cited

U.S. PATENT DOCUMENTS

| | | | |
|---|---|---|---|
| 6,171,317 B1 | 1/2001 | Jackson | |
| 6,978,176 B2 | 12/2005 | Lattouf | |
| 7,235,086 B2 * | 6/2007 | Sauer | A61B 1/0014 606/151 |
| 7,635,386 B1 | 12/2009 | Gammie | |
| 2003/0065338 A1 | 4/2003 | Takamoto | |
| 2003/0204205 A1 | 10/2003 | Sauer | |
| 2004/0097865 A1 * | 5/2004 | Anderson | A61B 17/0467 604/22 |
| 2005/0209612 A1 * | 9/2005 | Nakao | A61B 17/062 606/144 |
| 2006/0122633 A1 | 6/2006 | To | |
| 2008/0097479 A1 | 4/2008 | Boehlke | |
| 2008/0140093 A1 | 6/2008 | Stone | |
| 2008/0249545 A1 | 10/2008 | Shikhman | |
| 2010/0191254 A1 | 7/2010 | Wright | |
| 2011/0251641 A1 | 10/2011 | Sauer | |
| 2012/0053599 A1 | 3/2012 | Shikhman | |
| 2012/0131983 A1 | 5/2012 | Wotton | |
| 2012/0204865 A1 * | 8/2012 | Filipi | A61B 17/06061 128/200.26 |
| 2012/0283749 A1 | 11/2012 | Sauer | |

OTHER PUBLICATIONS

Mar. 29, 2009 Journal; Ruyra-Baliarda, Xavier, "Preliminary Experience with the No Prolapse System. A new device for ensuring the prior length of artificial chordae in mitral valve repair.", Interactice Cardiovascular and Thoracic Surgery; See pp. 165-167, in vol. 10, from issue , as published by in.

Jan. 1, 2010 Journal; Seeburger, Joerg , "Loop Technique", Multimedia Manual of Cardio Thoracic Surgery, doi:10,1510/mmcts. 2010.004523; See pages , in volume , from issue , as published by in.

Apr. 15, 2011 Journal; Isoda, Susoma , "The 'Loop with Anchor' Technique to Repair Mitral Valve Prolapse," Ann Thorac Cardiovasc Surg; See pp. 170-173, in vol. 18, from issue , as published by in.

Dec. 19, 2013 PCT International Patent Application Search Report for PCT patent application PCT/US2013/061522, mailed to Applicant dated Dec. 19, 2013.

Jul. 29, 2014 Office Action for Non-Provisional U.S. Appl. No. 13/840,481, mailed to applicant dated Jul. 29, 2014.

* cited by examiner

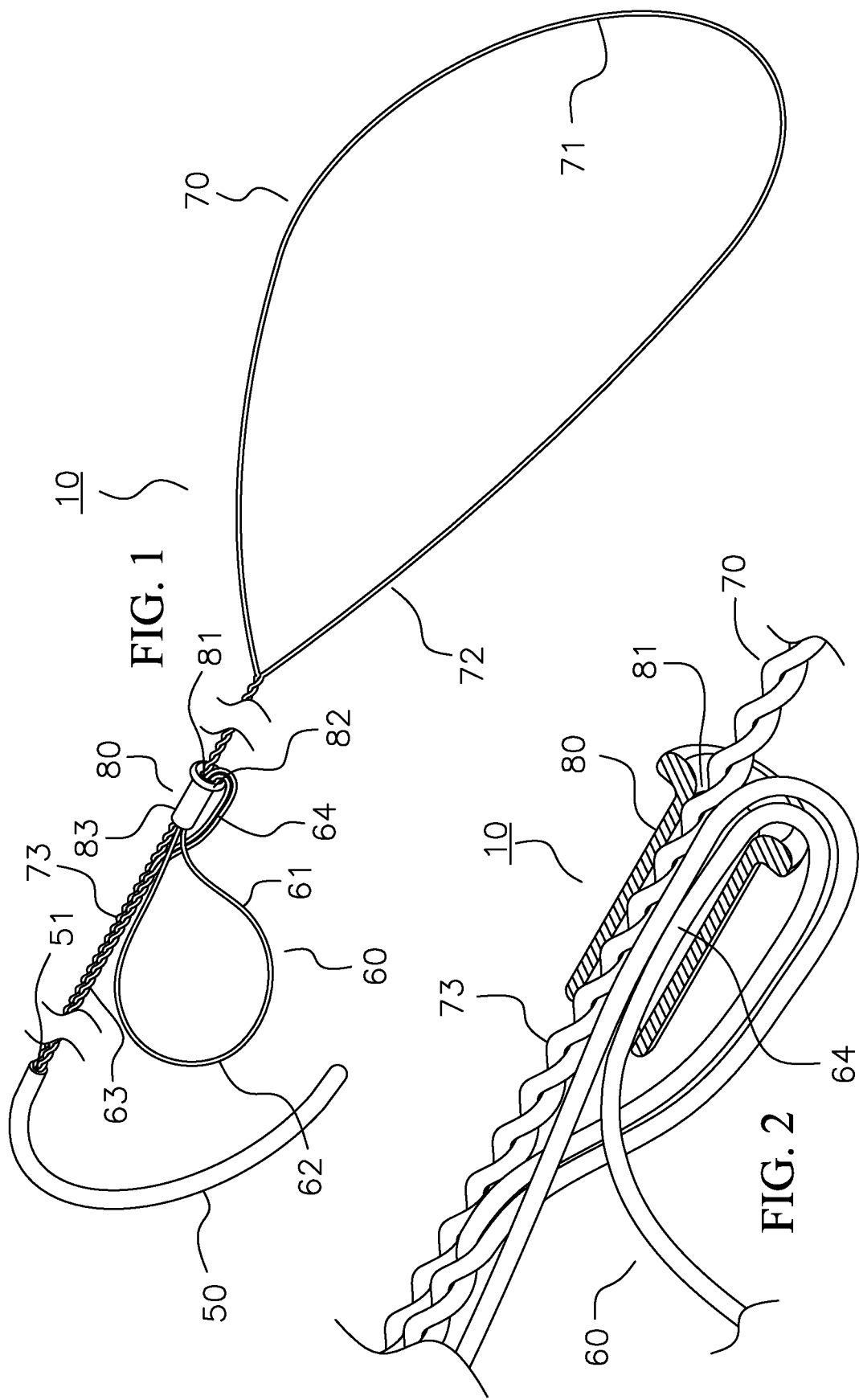

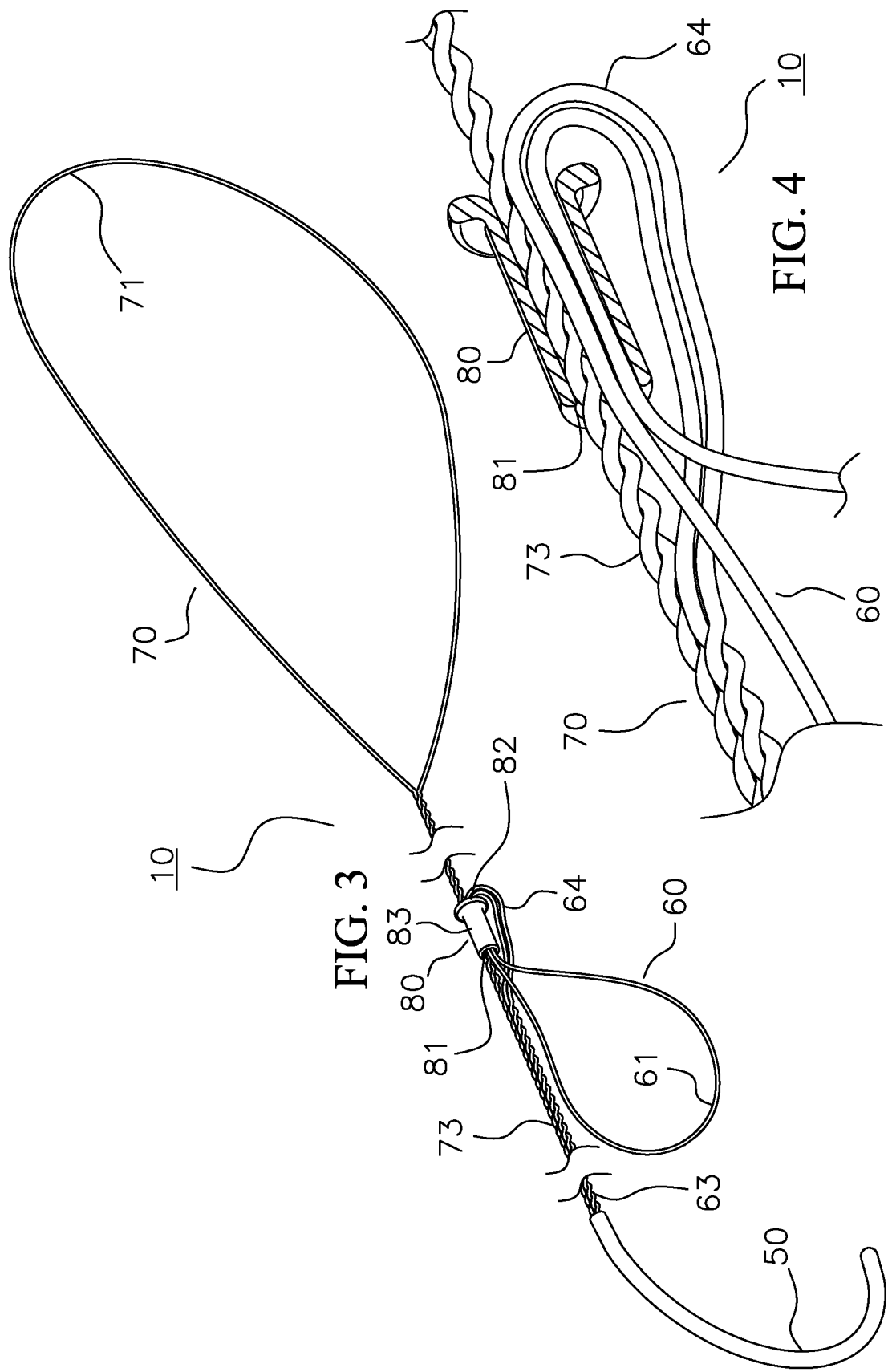

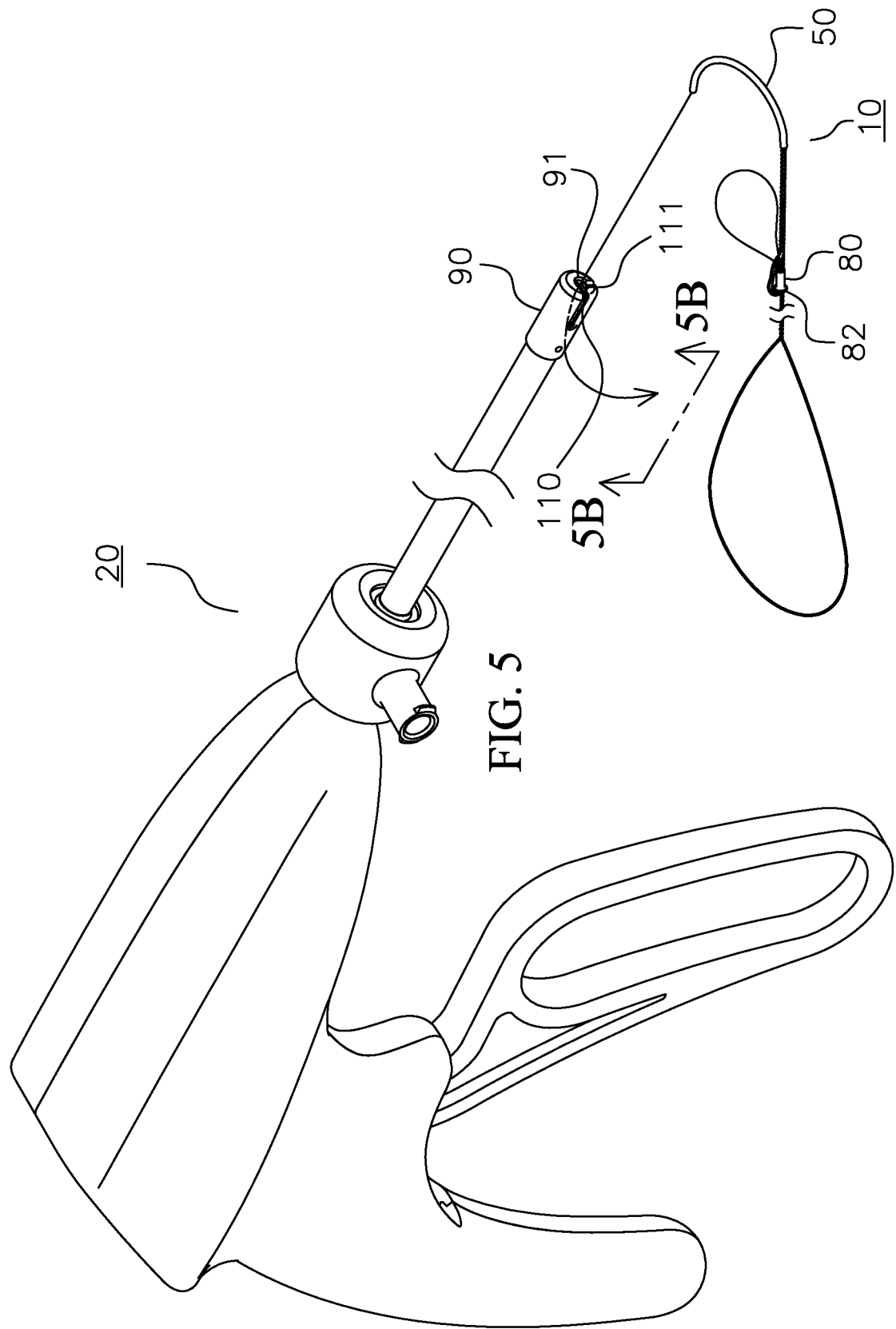

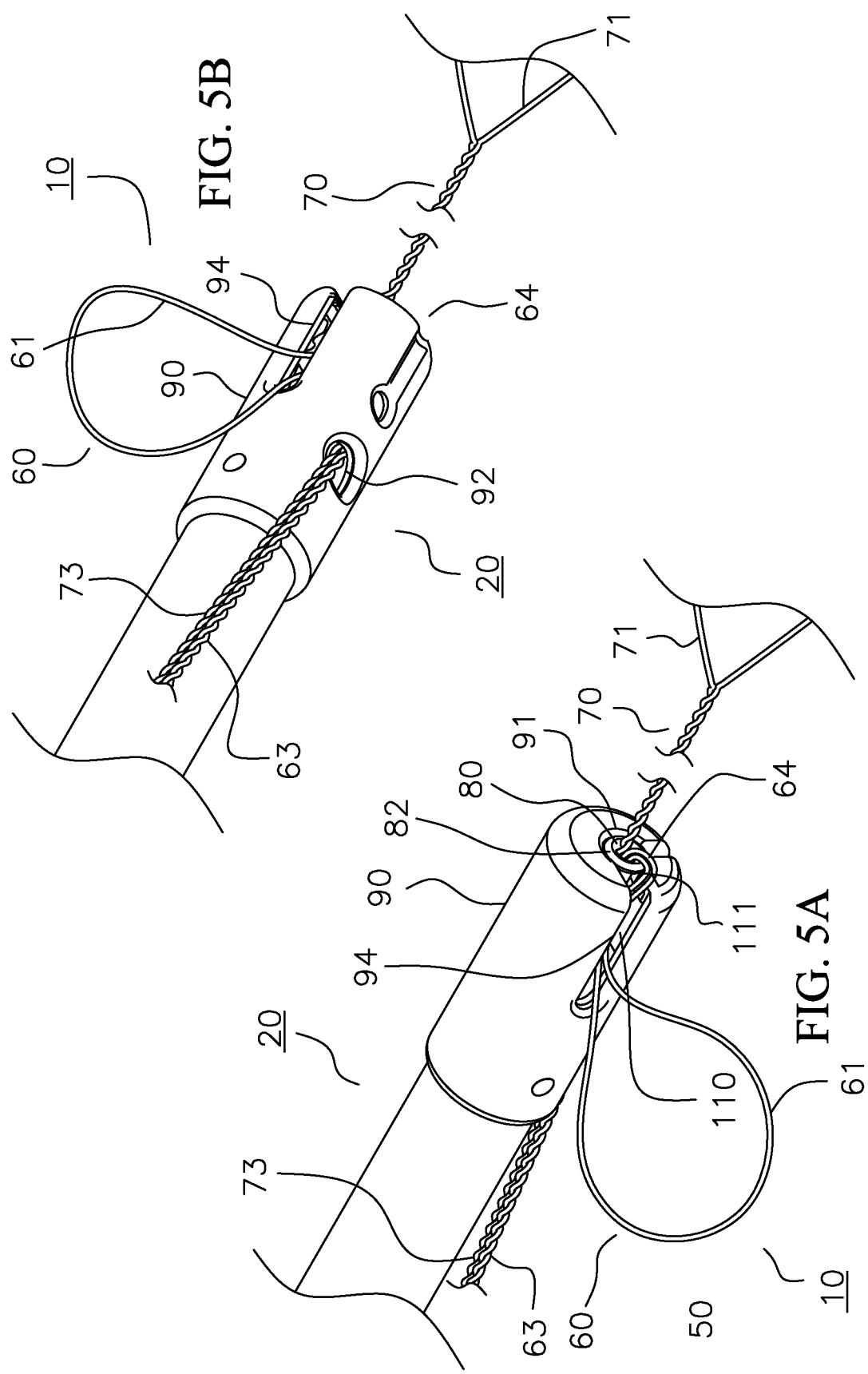

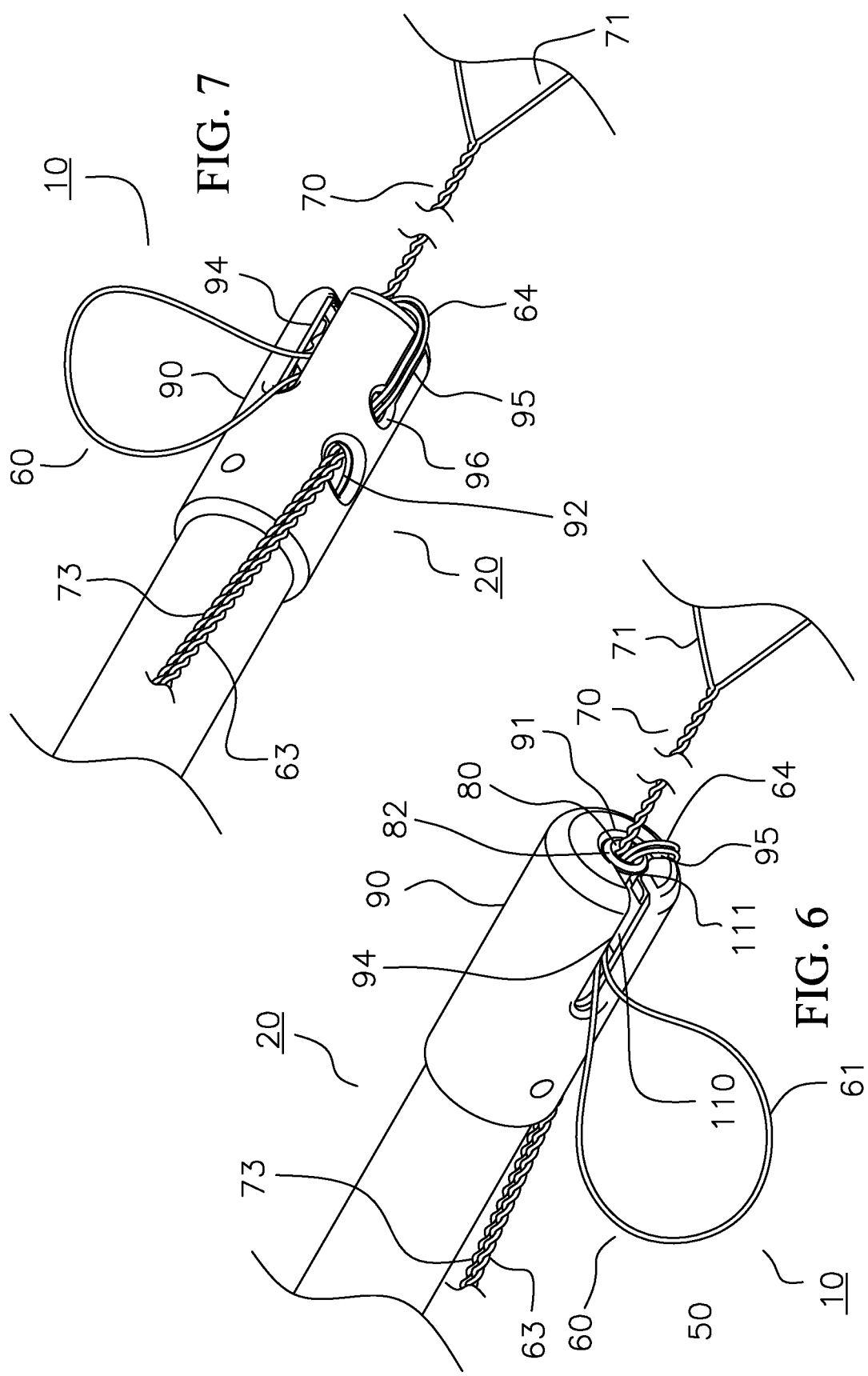

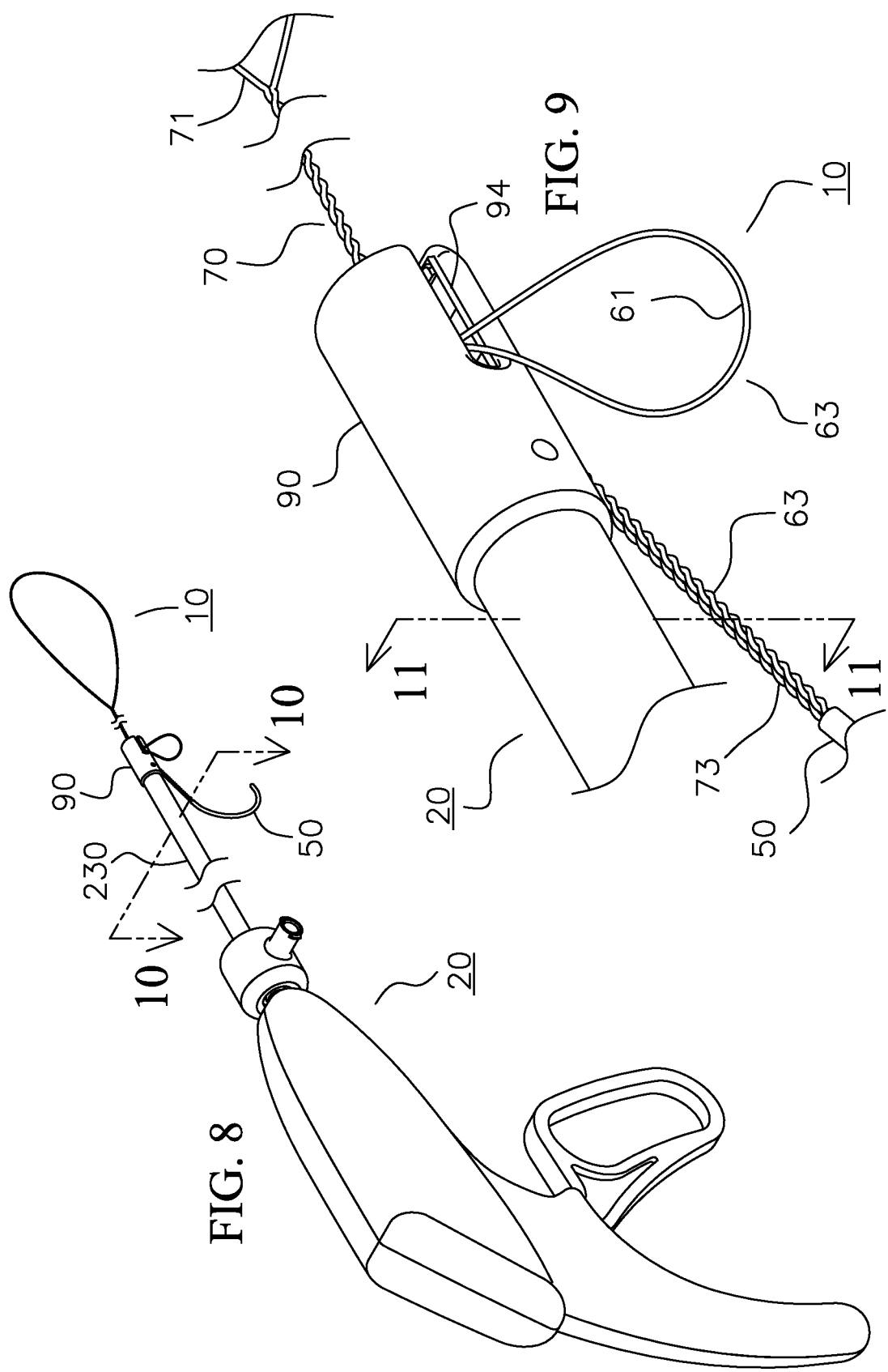

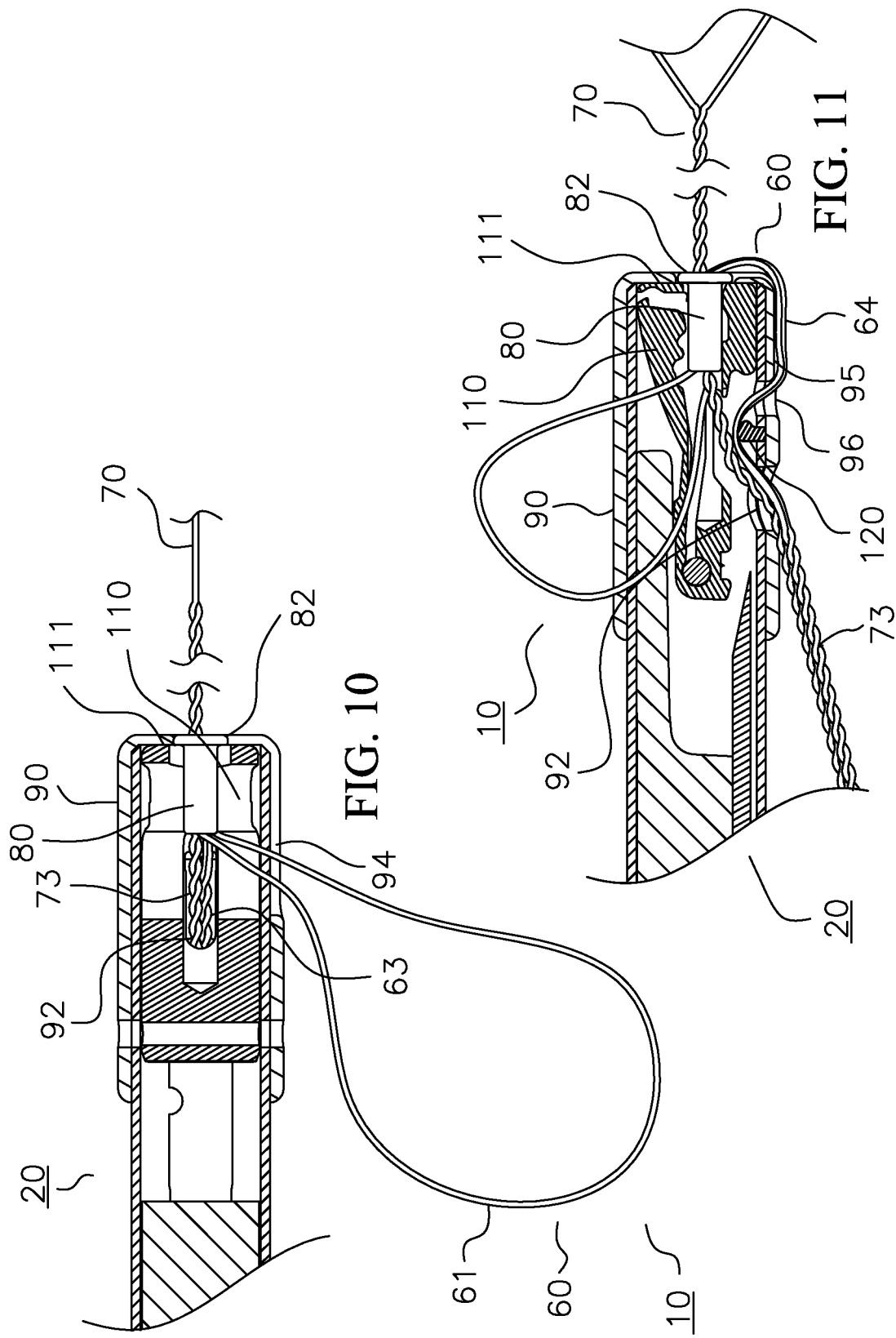

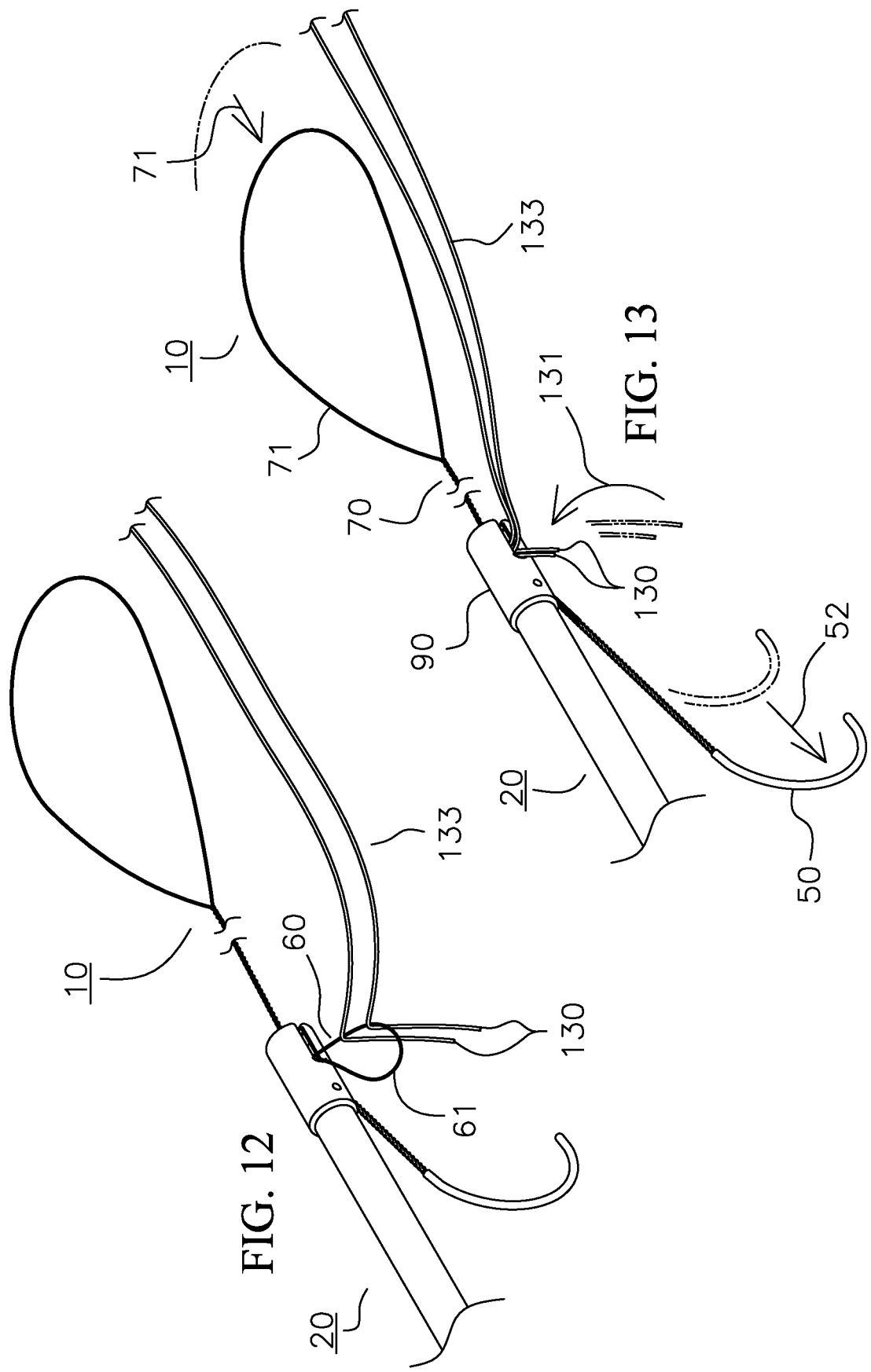

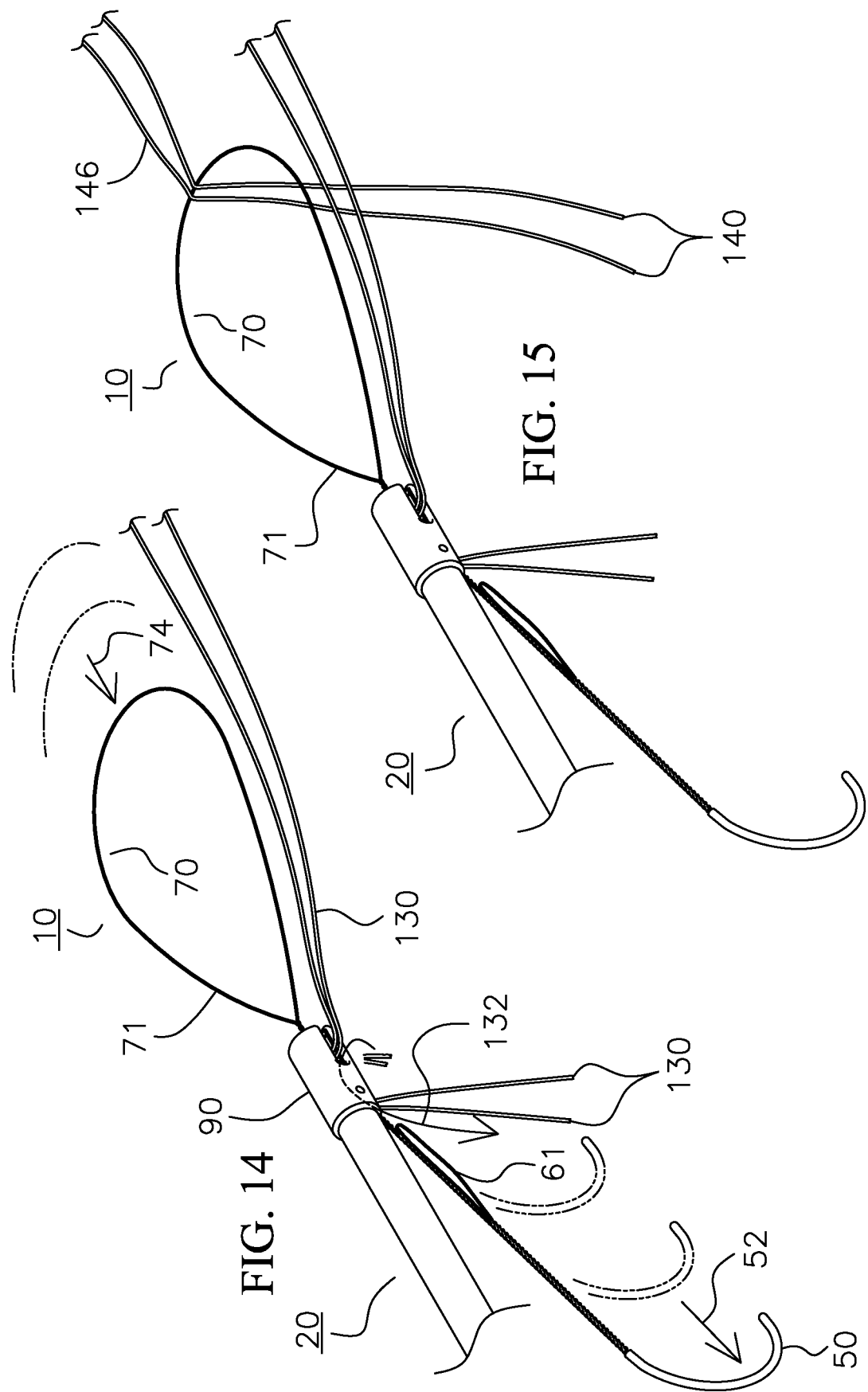

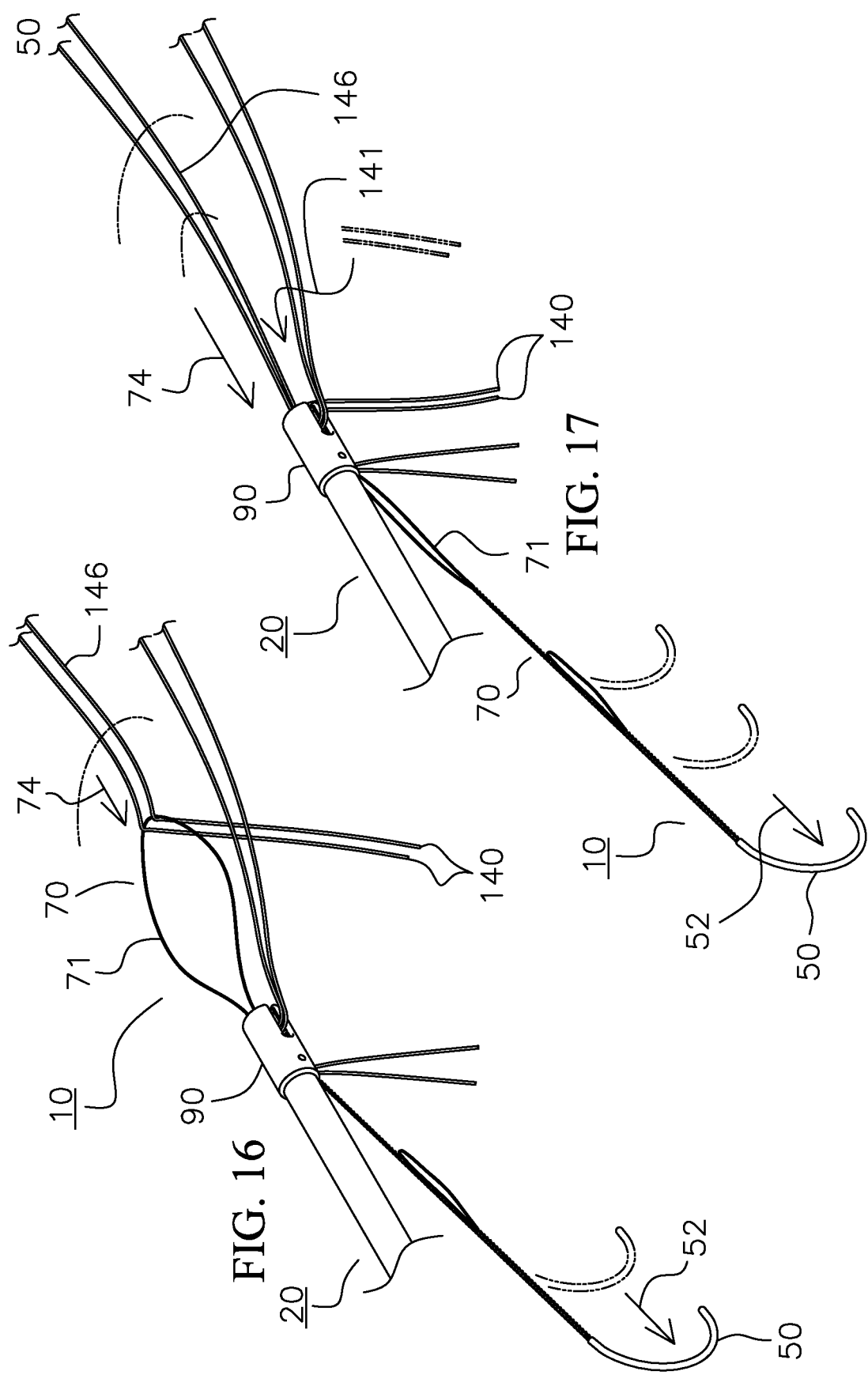

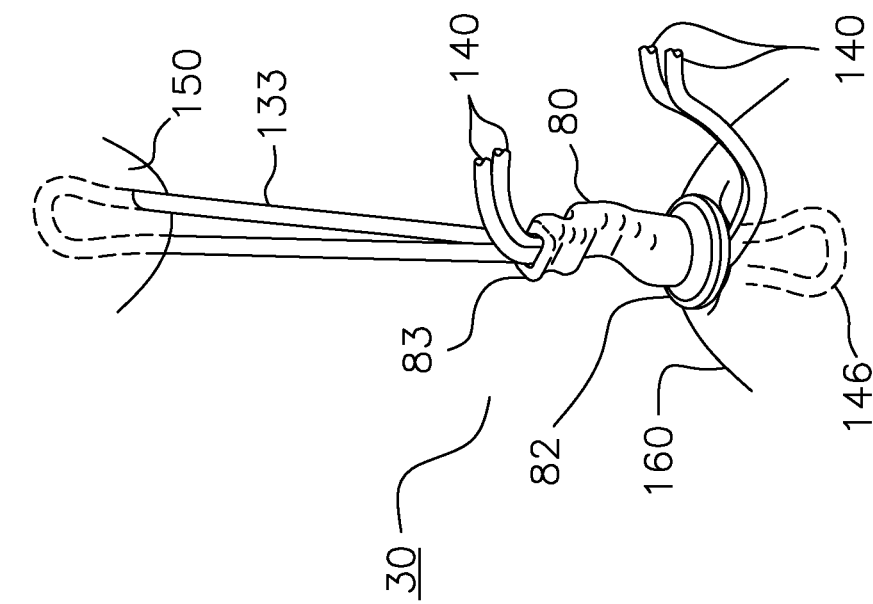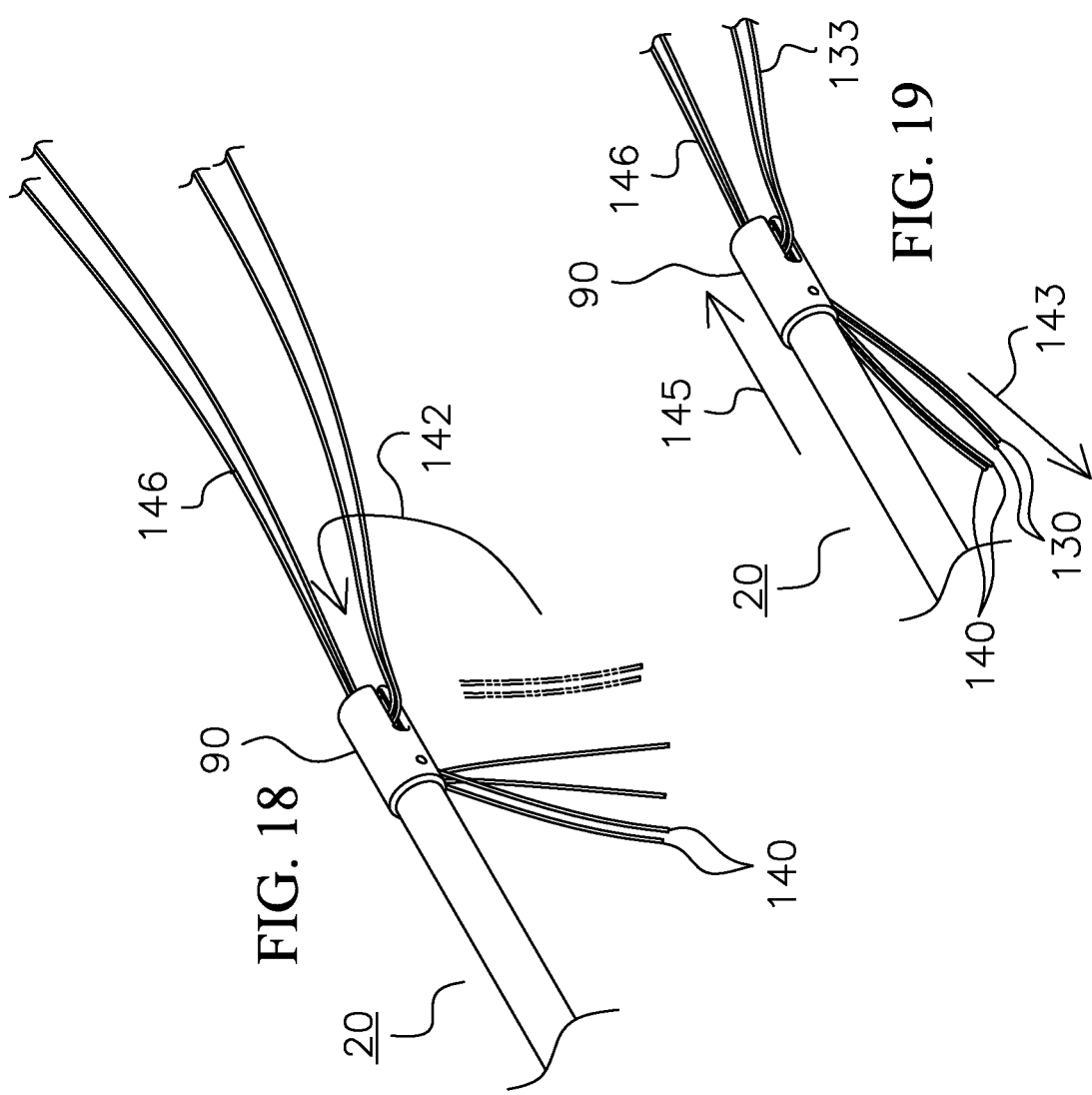

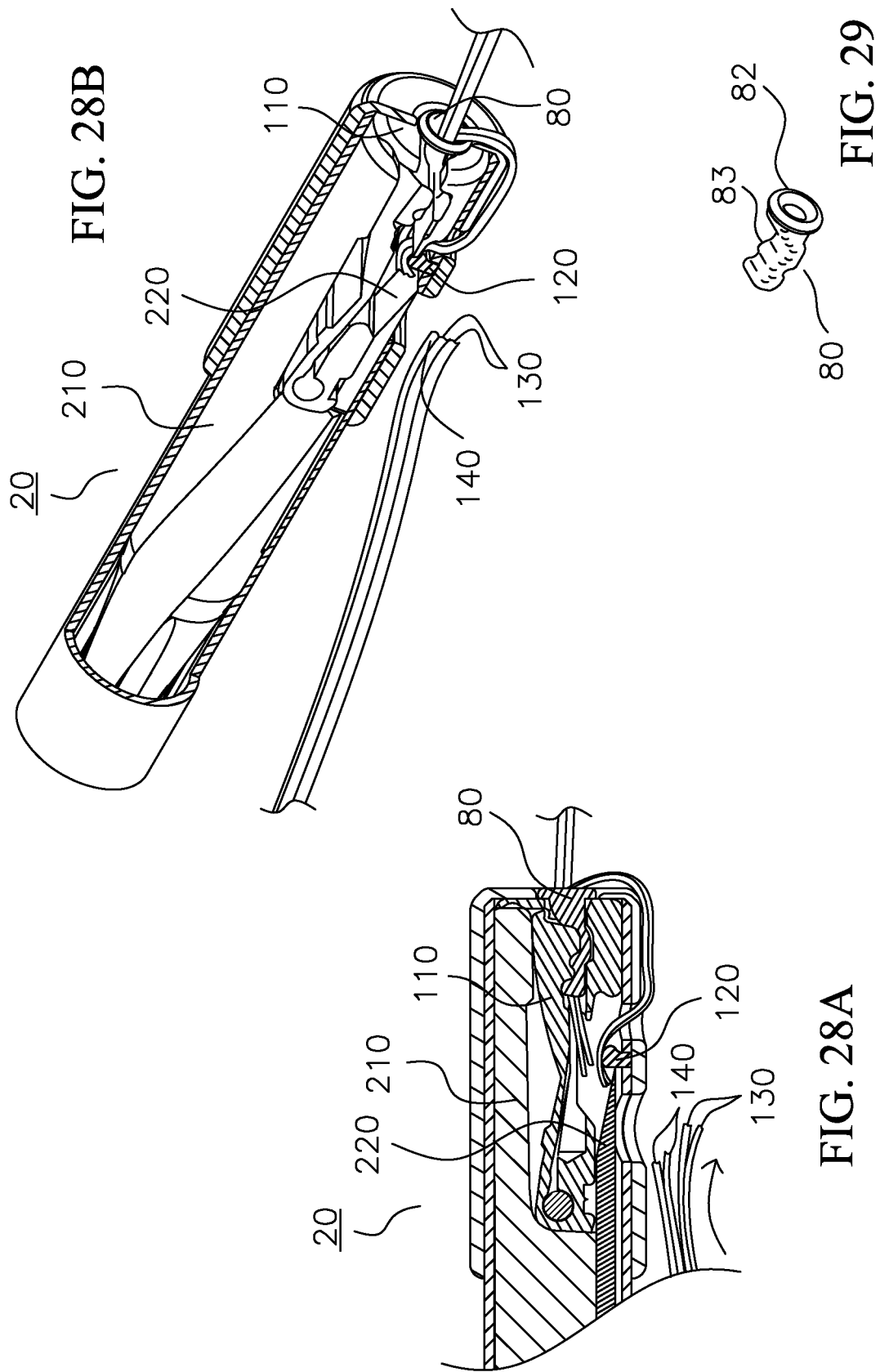

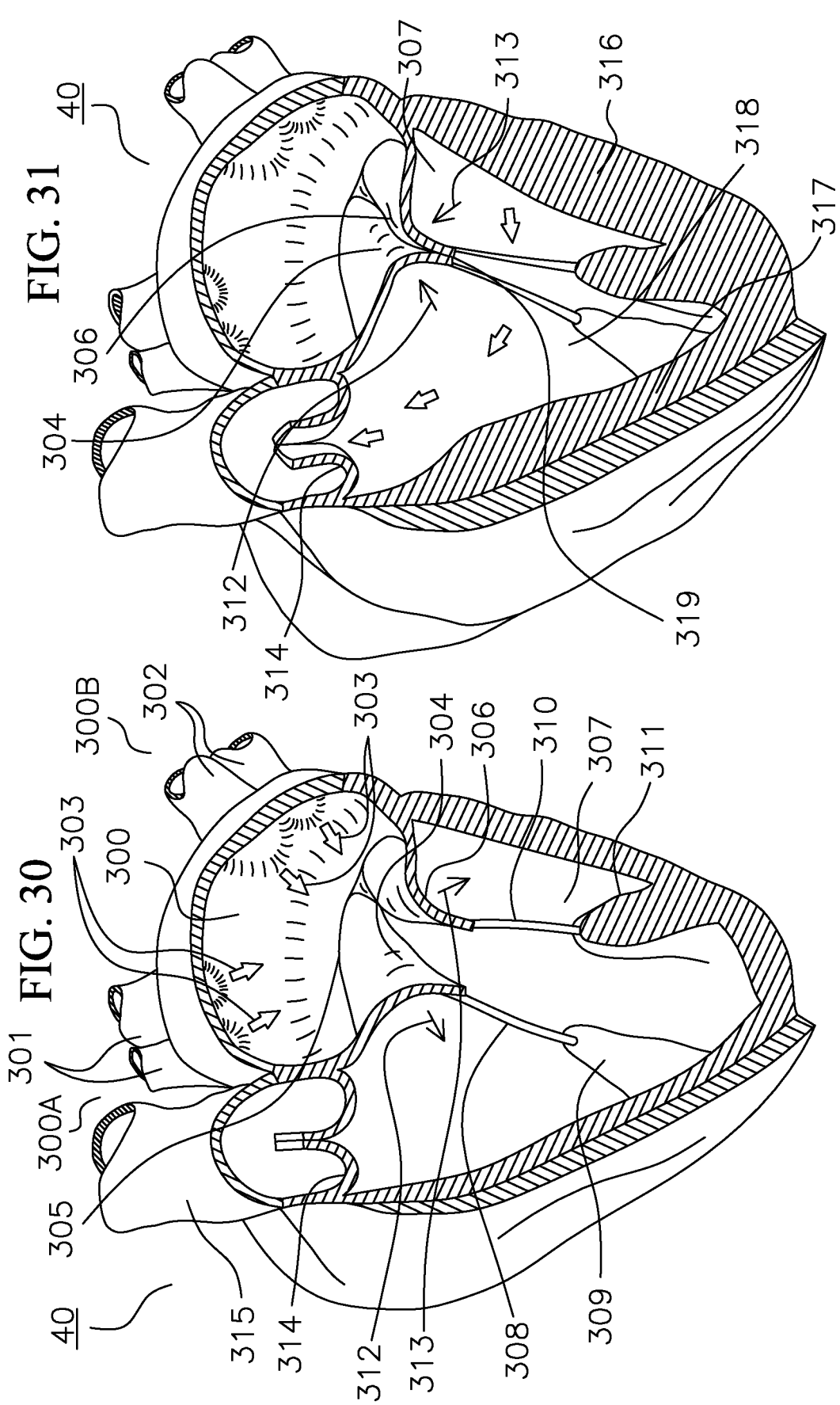

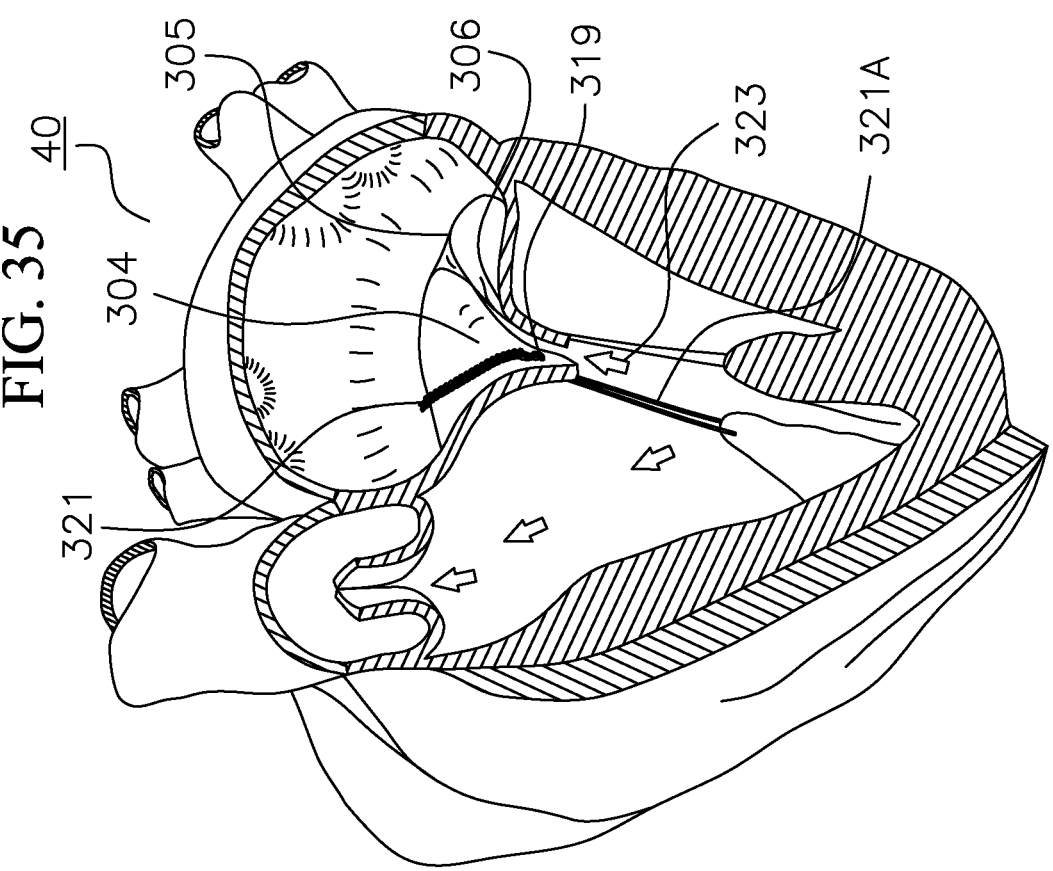
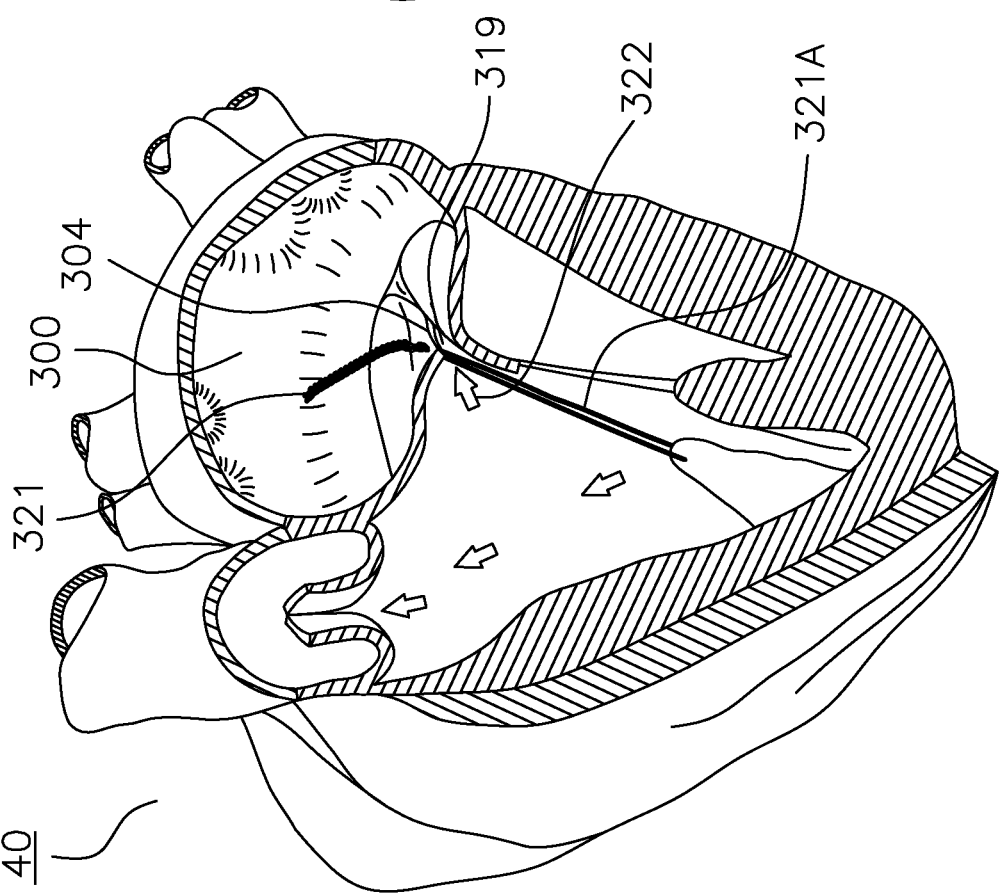

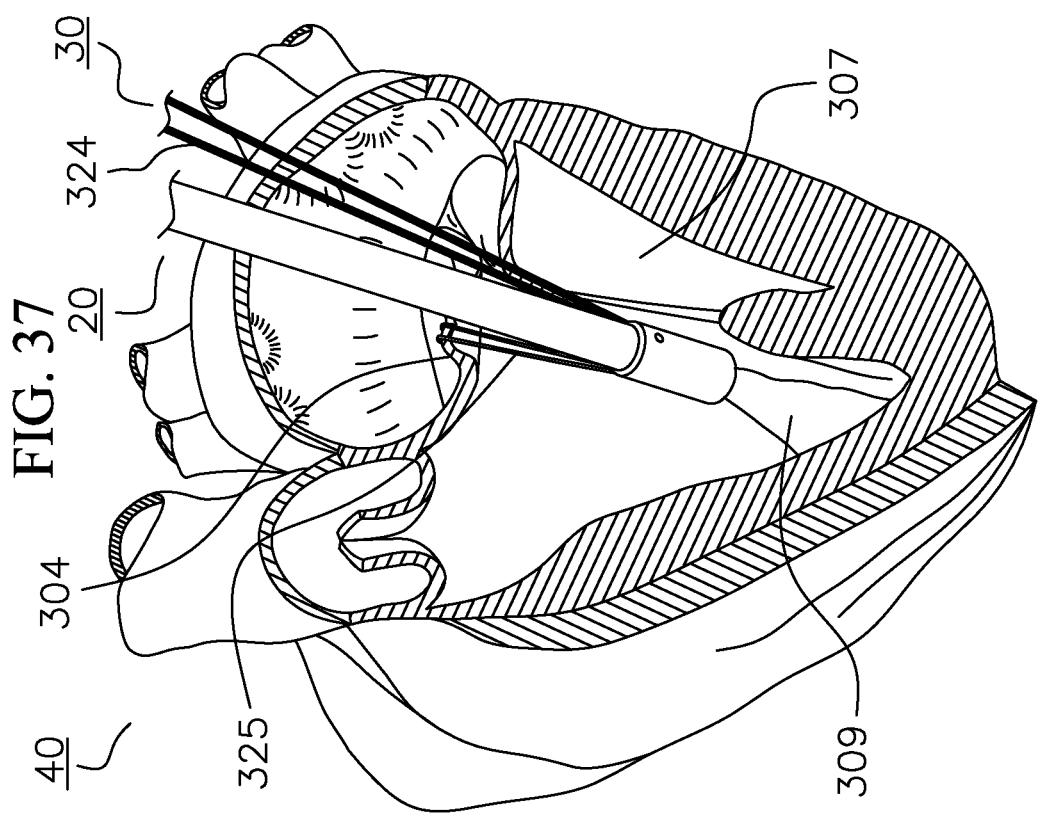
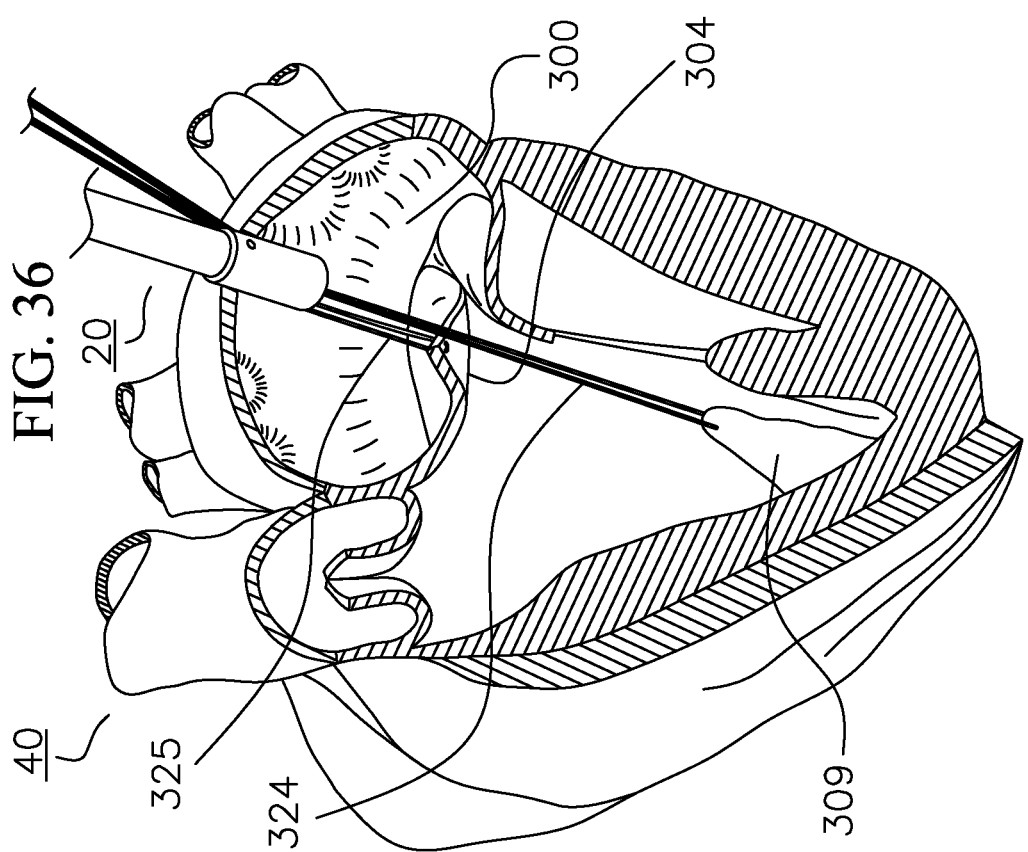

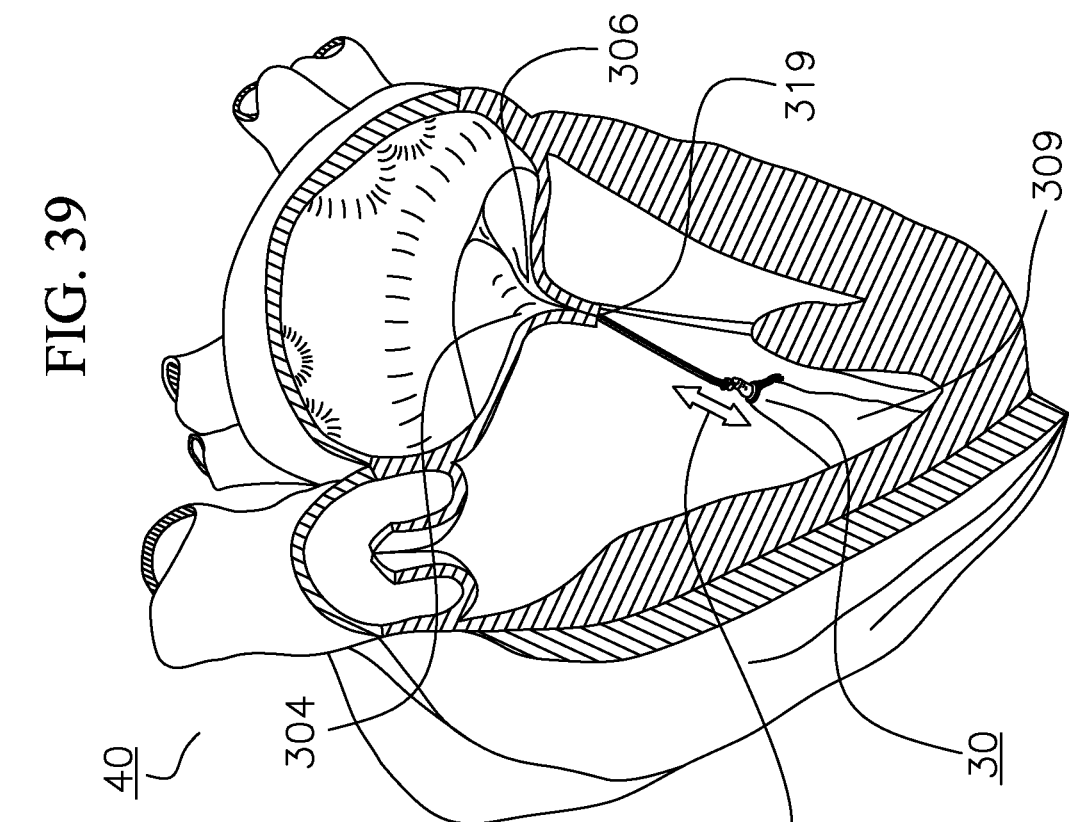
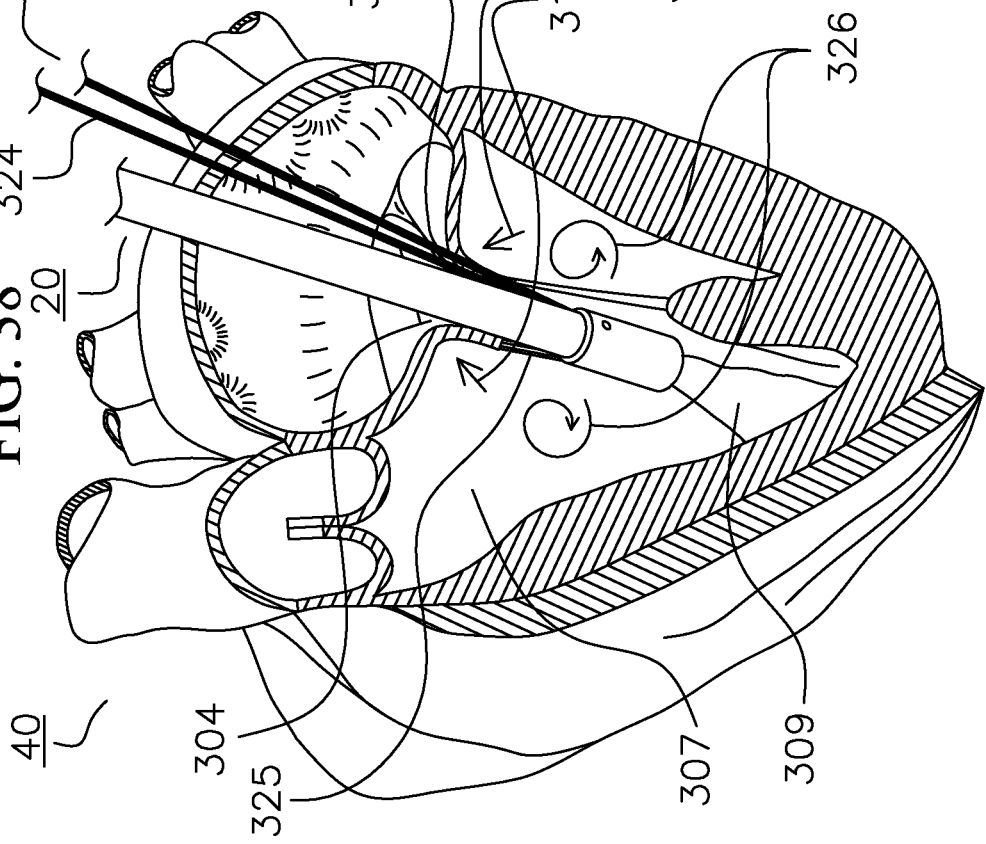

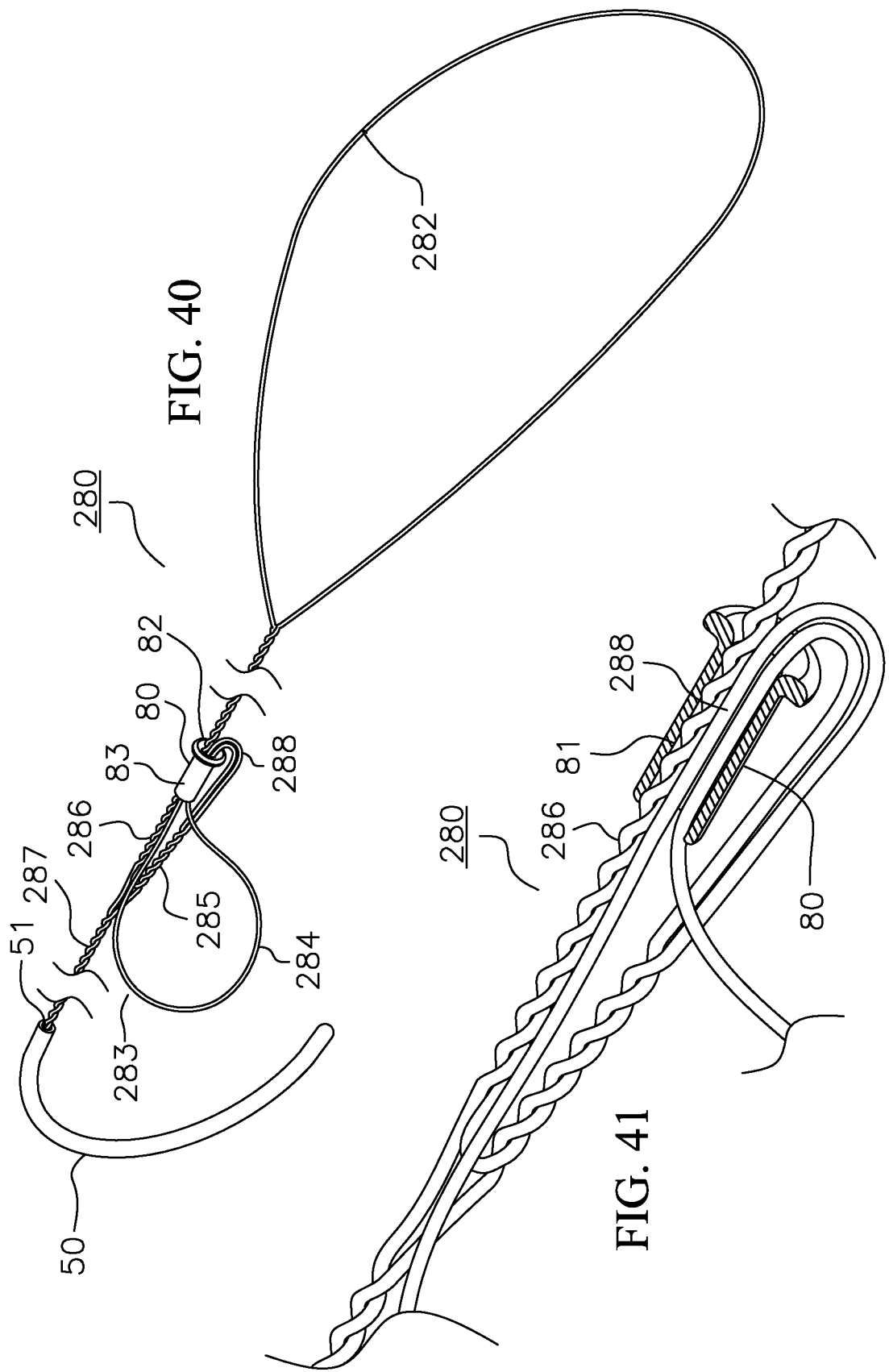

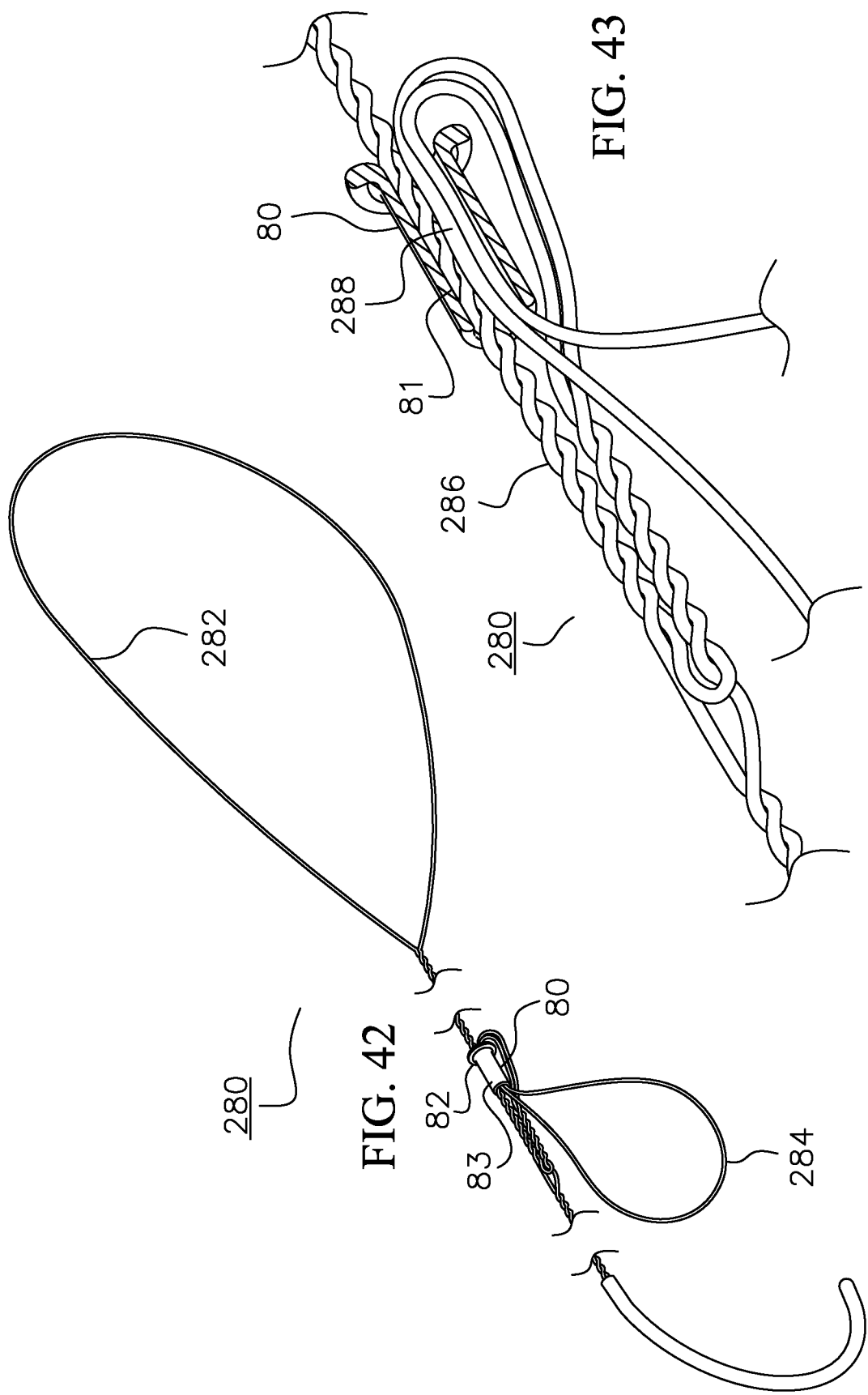

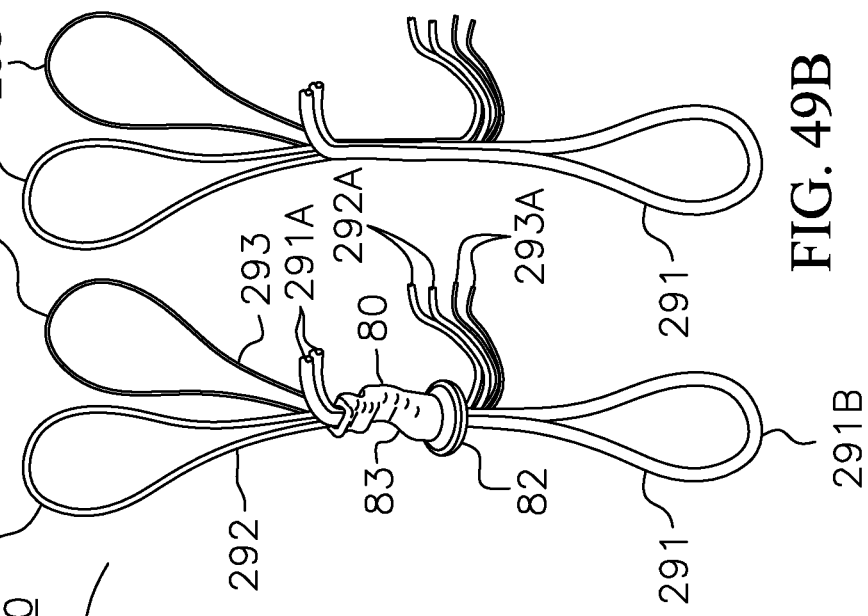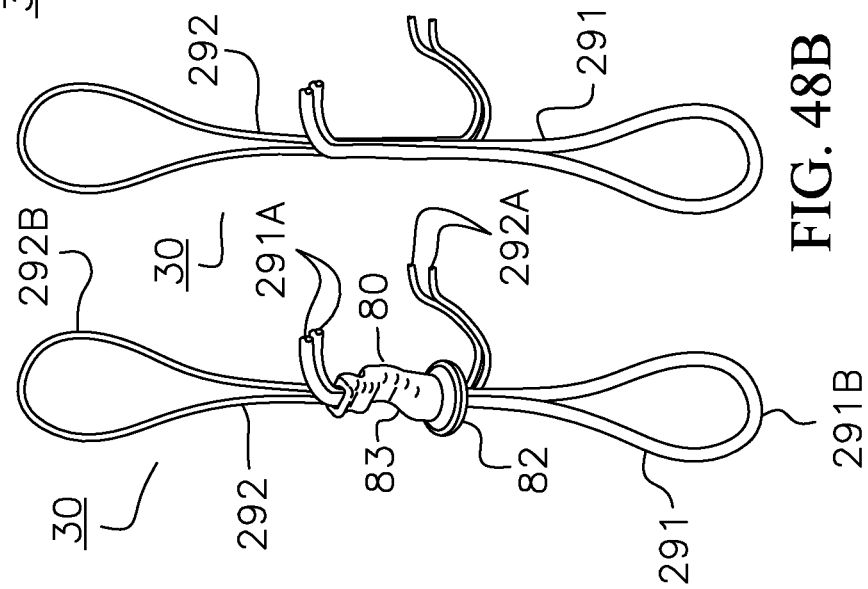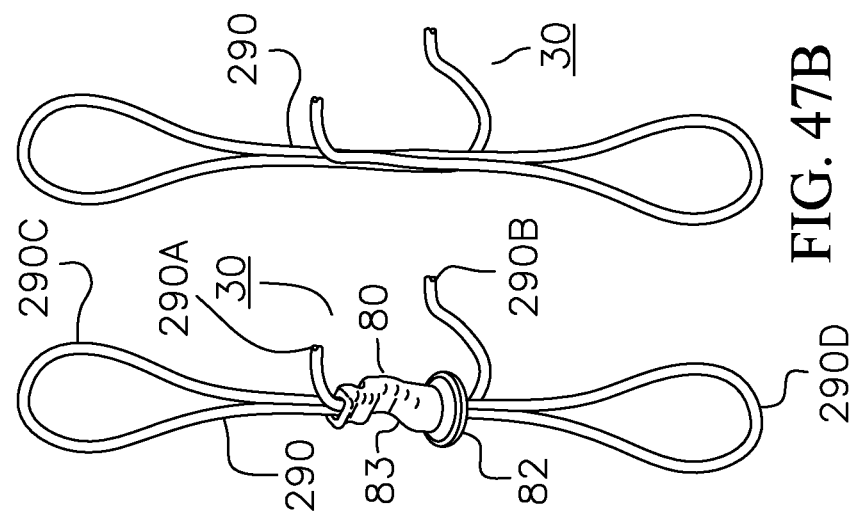

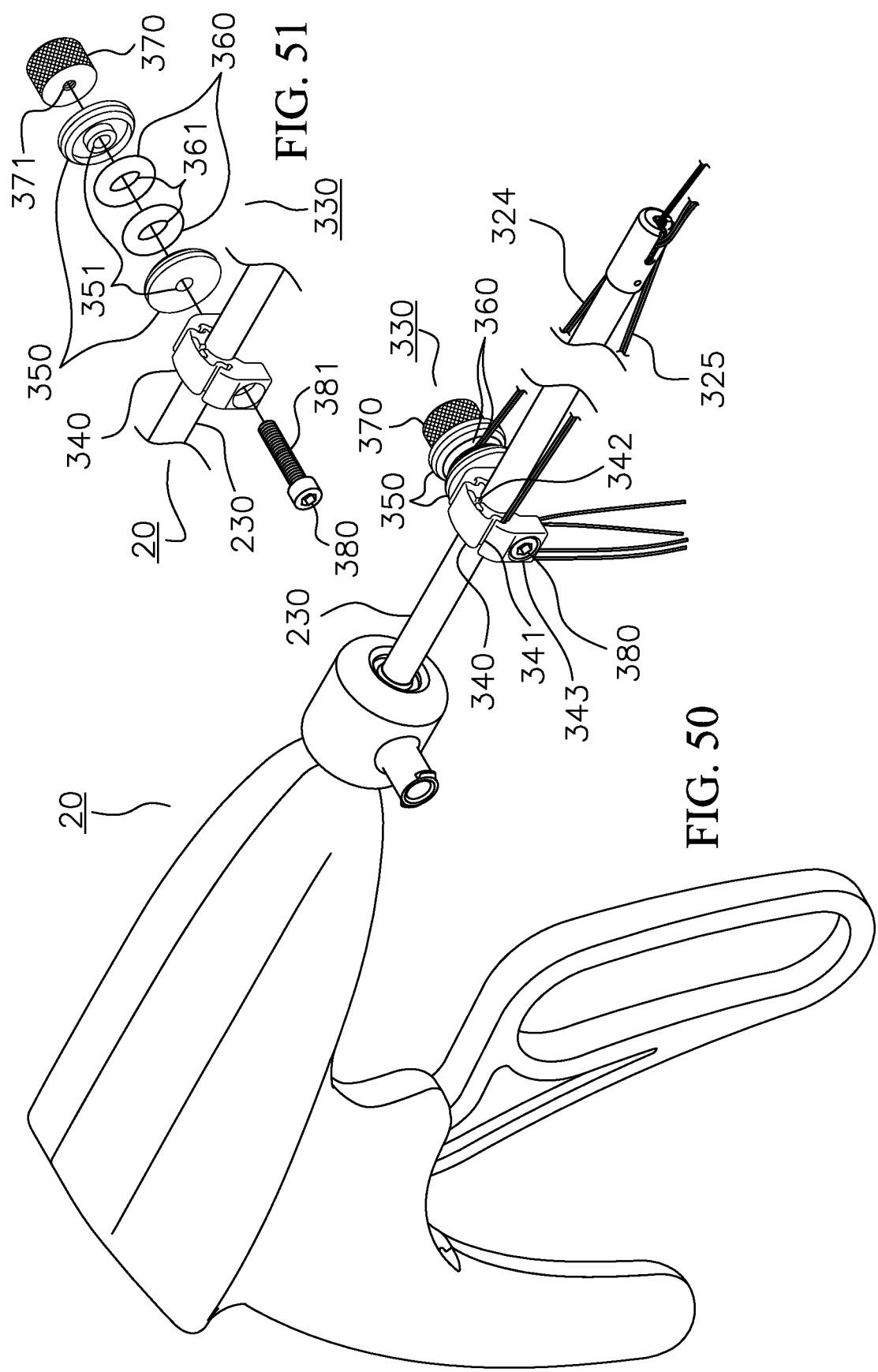

SECURING BIDIRECTIONAL SUTURE LOOPS USING COAXIAL FASTENERS

FIELD OF THE INVENTION

The use of a mechanical fastener or "knot" to secure or connect together a loop of surgical suture can provide an accepted alternative to the hand tying of a manual knot. Unlike a hand-tied manual knot, which is composed only of multiple throws of the suture itself, a mechanical suture fastener leaves behind inside of the patient another structural element in addition to the suture. Therefore, to be useful a mechanical fastener must be safe and ergonomic to deploy on the suture and present minimal risk to the patient's long-term clinical outcome. Inadvertent damage by the mechanical fastener to the placed suture or injury to the tissue or surrounding tissue structures is unacceptable.

Alternative knot replacement techniques and technologies to obviate the need for hand tying include sutures provided with pre-tied knots, barbed sutures, unidirectional cable ties or other mechanisms with integrated latching features.

An example of a simple mechanical fastener to help secure suture is seen in the use of generally V-shaped metal or plastic clips, sometimes called hemoclips. Such V-shaped clips can be placed around suture segments and then compressed together to hold suture strands together or to augment hand-tied knots. This type of clip application to suture often proves unreliable because stress concentrations on the suture in the narrow compression zone can lead to suture breakage and inadequate clip compression readily allows suture slippage.

An example of a more customized commercially available product uses a hollow titanium sleeve compressed or crimped around suture to hold two sections of suture within the crimped sleeve to preclude the strands of suture from slipping relative to each other. (TK™ Device, Ti-KNOT® titanium knots, LSI SOLUTIONS®, Victor, NY; U.S. Pat. Nos. 5,520,702; 5,643,289; 5,669,917; 5,766,183; 6,368,344; 6,641,592; 6,997,931; 7,235,086; 8,398,680). This titanium mechanical fastener is held circumscribed in the distal end of a customized surgical instrument. Both of the cut ends from a single strand of suture are pulled through the distal end of the device, while they are simultaneously pulled from the distal end of the mechanical fastener through its internal channel and out its proximal end. As the suture ends are pulled away from the fastener, the loop of suture at the distal end of the fastener is reduced in diameter. Suture can be placed around a tissue structure or through one or more tissue structures so that the closing loop described at the distal end of the titanium fastener draws the tissue together for compression or apposition. Compressing the mechanical fastener secures the suture within the fastener to hold the tissue in its desired position.

With this type of unidirectional hollow mechanical fastener holding a closed loop of suture, the fastener itself essentially becomes oriented perpendicular to the axis of the suture upon crimping. In other words, the two segments of suture coming into the distal end of the mechanical fastener are under tension in the opposite direction from each other and are thus splayed out in a linear orientation perpendicularly to the fastener. In most clinical applications, this non-coaxial fastener orientation does not compromise the wound closure or surrounding tissue structures. The technique of bringing together tissue through the use of a closed loop of suture held with a perpendicular fastener has become an accepted means of holding tissue or enabling wound closure in many surgical applications. Suture secured with a mechanical fastener can also be used to hold tissue against a surgical prosthetic material such as a hernia mesh or heart valve sewing ring. (CK™ Device, COR-KNOT® titanium knots, LSI SOLUTIONS® Victor, NY).

Over the past decade, this single loop mechanical fastener technology has been successfully used in many surgical applications such as for ligating blood vessels or for wound closures in tissues ranging from stomach to intestine to bladder. Until this current invention, mechanical fasteners were only envisioned for use to secure one strand of suture exiting from one end of the fastener yielding a single (i.e., unidirectional) closing suture loop and a perpendicularly oriented mechanical fastener.

In some critical surgical applications, if the mechanical suture fastener extends perpendicularly away from the tensioned suture towards adjacent structures, surrounding tissue structures or prosthetic materials may be subjected to an unacceptable risk of damage. In some heart surgery procedures, it may be very desirable to have a minimal profile coaxial fastener to connect more than one loop of suture exiting at either end of this fastener (i.e., bidirectional plurality of loops). For example, there is no known fastener that can be used to safely connect the papillary muscles to the mitral leaflets with suture.

The human heart has four chambers and four valves. The upper chambers, called the right atrium and left atrium, receive blood coming to the heart from the systemic venous circulation and from the pulmonary veins, respectively. The lower, more muscular, chambers of the heart pump blood back from the heart towards the lungs through the right ventricle and towards the systemic circulation from the left ventricle. The right and left atria receiving chambers are separated from their respective right and left ventricles by two separate atrial valves, called the tricuspid and mitral valves, respectively. Atrial valves have cusps or leaflets that are held like parachutes by cord-like attachment structures, called chordae tendineae. These valve leaflets open during diastole when blood flows through the atria toward the ventricle and close to preclude blood passage back into the atria during systole when heart contraction occurs. The chordae tendineae structures help prevent valve leaflet prolapse (i.e., pathologic excessive movement) by connecting valve leaflets to muscular projections in the ventricles called papillary muscles. (Chordae tendineae structures are not part of the pulmonary valve at the exit of the right ventricle or the aortic valve at the left ventricle; these valves preclude return of blood from the lungs and body, respectively.) Atrial valves occur in a wide variety of shapes and sizes. Common heart valve disease processes often involve elongation or disruption of atrial valve chordae tendineae, which can lead to leaky heart valves.

The purpose of this disclosure is to address the need for improved chordae tendineae replacement during atrial valve repair. Better technology and methods for real time evaluation of the correct suture length for replacement chordae tendineae under functional surgical conditions could help many patients. Precise replacement of damaged native chordae tendineae can re-establish proper atrial valve closure.

Recent advances in minimally invasive cardiac surgery have enabled remote access to diseased tricuspid and mitral heart valves. For simplicity herein, we will focus only on the mitral valve subsequently in this document. Surgeons have recognized the need for alternative techniques and technologies to provide better options for repairing pathologic mitral valve chordae tendineae. The routine repair of damaged or torn mitral valve chordae tendineae requires placement with a suture (typically a Gore-Tex® suture, W. L. Gore &

Associates, Flagstaff, AZ) through the mitral leaflet and the adjacent papillary muscle. Hand tying of this thin and slippery suture remains an extremely unreliable technical challenge, especially during minimally invasive cardiac surgery. Bulky hand-tied knots are routinely left at the coaptation zone between the leaflets of the mitral valve and could theoretically interfere with valve leaflet closure. While the anatomic distance between the leaflet and papillary muscle can range from 1 to 2.5 cm, depending on the intraoperative heart's shape and size, each individual valve repair requires a precise suture length to enable proper leaflet alignment and valve function. Since chordae tendineae replacement sutures often are tied too long or too short and once tied cannot be adjusted, they are frequently cut out, resutured and retied.

DESCRIPTION OF RELATED ART

Several suboptimal alternatives for mitral chordae tendineae replacement have been offered by other investigators.

A technique incorporating multiple pre-tied suture loops of a predetermined length and arranged in a series usually of four loops tied into a single suture is used by a limited number of surgeons. This pre-tied suture loop configuration approach to chordae tendineae replacement was first described around 2000 by Drs. von Oppell and Mohr in Leipzig, Germany. While this pre-tied loop approach purports to enable more reliable suture lengths between the leaflets and papillary muscle, it requires an elaborate measurement technique to determine the length the loop should be tied. First the pre-tied loop arrangement is anchored to the papillary muscle by placing suture and hand-tying a knot. Then, each individual loop is sutured and hand-tied usually using two additional sutures to each affected pre-tied suture loop. Because this pre-tied loop technique is complicated and challenging, and still requires significant remote suture placement and hand-tied knotting, this approach is generally limited to a few dedicated centers in Europe. Since 2010, mitral chordae tendineae replacement suture provided in various pre-set lengths with pre-tied loops are commercially available through Santech Medical, Grosswallstadt, Germany.

In 2012, Isoda et al reported a similar "Loop with Anchor" technique used in their patients for mitral valve prolapse. They describe the use of a rudimentary "handmade knot pusher . . . made from a funnel" which they placed over a finger to improve manual knot tying.

Ruyra-Balliarda published an article presenting a new surgical device for intraoperative use to aid in chordae tendineae replacement in ten patients beginning in 2007. This mechanical implement is temporarily sewn over the mitral valve to help establish replacement suture length and to preclude over tightening of the hand-tied knots.

Lattouf (U.S. Pat. No. 6,978,176 B2) describes accessing the mitral valve through the apex of the heart and left ventricle to use a grasper and balloon technique to orient mitral leaflets and subsequently place a clip at the coaptation zone of the leaflets.

Gammie (U.S. Pat. No. 7,635,386 B1) proposed a suturing technology and method for chordae tendineae replacement that again involves accessing the mitral valve through the left ventricle via the apex of the heart. Several alternative suture placement and knot replacement techniques are described. One embodiment of Gammie illustrates a plug to close the apex of the heart. This plug also acts as a suture fastener to secure a single loop of suture coming from the mitral valve leaflet to an attachment site on the cardiac apex. Gammie's described unidirectional mechanical suture fastener approach is similar to the aforementioned hollow, crimped titanium mechanical fastener in which a single loop of suture enters the distal apical plug and exits its proximal surface.

BRIEF SUMMARY OF THE INVENTION

With the availability of a mechanical fastener coaxial with one or more loops of suture coming from one end and an additional loop or loops of suture coming from the opposite end, the fastener could then ride essentially parallel to the suture strands, minimizing the fastener's profile and presenting a reduced risk for damaging adjacent structures. Such technology must be small enough to fit into confined remote surgical fields, reasonably atraumatic and provide a secure suture holding means. Both the fastener and connected strands of suture must be readily released from the deployment device.

This invention provides a means of securing separate loops of suture through a common mechanical fastener. Moreover this invention permits separate loops of suture to extend from opposite ends of the mechanical fastener to enable a coaxial mechanical fastener orientation relative to the bidirectional suture loops. Novel wire snare mechanisms that permit pulling of the suture through both ends of the fastener are also disclosed. This invention further permits the release of the wire snares, bidirectional mechanical fastener and sutures from the tip of the fastener securing device. One embodiment of this invention offers the infusion of pressurized physiologic solutions through the end of the mechanical fastener deployment device into the left ventricle so that the proper replacement suture length can be demonstrated real time under physiologic conditions prior to crimping the fastener. The fastener deployment device incorporates a slotted release site so that the knot and suture can be liberated from the device tip once the fastener is secured. A method of securing suture coming from cardiac valve leaflets and or other structures like papillary muscles is provided. This method permits a more atraumatic orientation of the fastener so it remains coaxial with the suture strands instead of perpendicular to the suture strands as seen in previous product.

BRIEF DESCRIPTION OF THE DRAWINGS

The foregoing objects, features and advantages of the invention will become more apparent from a reading of the following description in connection with the accompanying drawings in which:

FIG. 1 is a distally oriented perspective view of a bidirectional snare device as presented for use;

FIG. 2 is an enlarged partial section view of the bidirectional snare device presented in FIG. 1;

FIG. 3 is a proximally oriented perspective view of the bidirectional snare device of FIG. 1;

FIG. 4 is an enlarged partial section view of the bidirectional snare device presented in FIG. 3;

FIG. 5 is a distally oriented perspective view of the bidirectional snare device of FIG. 1 in preparation for use in a corresponding deployment device when applied to its field of use;

FIG. 5A is an enlarged top-frontal perspective view of the distal end of the deployment device of FIG. 5 with the installed bidirectional snare device of FIG. 1 as presented for use;

FIG. 5B is an enlarged bottom-rear perspective view of the deployment device of FIG. 5 along lines 5B-5B of FIG. 5 with the installed bidirectional snare device of FIG. 1 as presented for use;

FIG. 6 is an enlarged top-frontal perspective view of the distal end of the deployment device of FIG. 5C with the installed bidirectional snare device of FIG. 1 as presented for use;

FIG. 7 is an enlarged bottom-rear perspective view of the deployment device of FIG. 5 along lines 7-7 of FIG. 5C with the installed bidirectional snare device of FIG. 1 as presented for use;

FIG. 8 is a proximal perspective view of the deployment device of FIG. 5 with the installed bidirectional snare device of FIG. 1 as presented for use;

FIG. 9 is an enlarged top-rear perspective view of the distal end of the deployment device of FIG. 5 with the installed bidirectional snare device of FIG. 1 as presented for use;

FIG. 10 is a partial orthogonal section view along lines 10-10 in FIG. 8 of the deployment device of FIG. 5 with accompanying bidirectional snare device of FIG. 1;

FIG. 11 is a partial orthogonal section view along lines 11-11 in FIG. 9 of the deployment device of FIG. 5 with accompanying bidirectional snare device of FIG. 1;

FIG. 12 is a partial distally oriented rear perspective view of the deployment device with installed bidirectional snare device as shown in FIG. 8 in the preferred method of use accepting a first suture;

FIG. 13 is again a partial distally oriented rear perspective view of the deployment device of FIG. 8 illustrating the partial withdrawal of the bidirectional snare device of FIG. 1 and the subsequent progressed accommodation of the first suture first shown in FIG. 12;

FIG. 14 is again a partial distally oriented rear perspective view of the deployment device of FIG. 8 illustrating the further withdrawal of the bidirectional snare device of FIG. 1 and the subsequent exit of the first suture from the device of FIG. 8;

FIG. 15 is again a partial distally oriented rear perspective view of the deployment device of FIG. 8 with installed bidirectional snare device of FIG. 1 in the preferred method of use accepting a second suture.

FIG. 16 is again a partial distally oriented rear perspective view of the deployment device of FIG. 8 illustrating the further withdrawal of the bidirectional snare device of FIG. 1, first initiated in FIG. 12, and the subsequent progressed accommodation of the second suture first shown in FIG. 15;

FIG. 17 is again a partial distally oriented rear perspective view of the deployment device of FIG. 8 illustrating the almost entire withdrawal of the bidirectional snare device of FIG. 1, first initiated in FIG. 12, and the subsequent progressed accommodation of the second suture;

FIG. 18 is a partial distally oriented rear perspective view of the deployment device of FIG. 8 illustrating the fully accommodated and exiting first and second sutures introduced in FIGS. 12 and 16, respectively;

FIG. 19 is a partial distally oriented rear perspective view of the deployment device of FIG. 5C advancing while opposing tension is applied to the exited first and second sutures shown in FIG. 18;

FIG. 20 is a perspective view of the first and second sutures as applied to tissue in the intended field of use and referred to as a coaxial mechanical fastener;

FIG. 28A is a partial orthogonal section view along lines 11-11 in FIG. 9 of the deployment device of FIG. 5C again illustrating the crimping of the sleeve around suture and the trimming of said suture;

FIG. 28B is an alternate enlarged perspective view of the distal portion of the deployment device from FIG. 26 again illustrating the crimping of the sleeve around suture and the trimming of said suture;

FIG. 29 is a distal view of a crimped sleeve as produced by the action of the device in FIG. 26;

FIG. 30 is a partial section schematic view illustrating the human heart in diastole with the left front side removed;

FIG. 31 is a partial section schematic view illustrating the human heart in systole with the left front side removed;

FIG. 34 is a partial section schematic view illustrating the human heart in systole with the left front side removed highlighting a replacement suture tied too long on the anterior leaflet of the mitral valve;

FIG. 35 is a partial section schematic view illustrating the human heart in systole with the left front side removed highlighting a replacement suture tied too short on the anterior leaflet of the mitral valve;

FIG. 36 is a partial section schematic view illustrating the human heart in systole with the left front side removed with a suture loop from the papillary muscle and another suture loop from the mitral anterior leaflet both passing through the distal end of the deployment device upon its entry into the left atrium;

FIG. 37 is a partial section schematic view illustrating the human heart in systole with the left front side removed showing a suture loop from the papillary muscle and another suture loop from the mitral anterior leaflet both passing through the distal end of the deployment device which is now seated on a papillary muscle in the left ventricle;

FIG. 38 is a partial section schematic view illustrating the human heart in systole with the left front side removed with the deployment device seated on a papillary muscle and infusing saline into the left ventricle with the suture chordae tendineae replacement now set to the correct length;

FIG. 39 is a partial section schematic view illustrating the human heart in systole with the left front side removed showing the fully emplaced coaxial mechanical fastener of FIG. 20 holding sutures and the proper leaflet coaptation as set in FIG. 38;

FIG. 40 is a distally oriented perspective view of an additional embodiment of a bidirectional snare device as presented for use;

FIG. 41 is an enlarged partial section view of the bidirectional snare device presented in FIG. 40;

FIG. 42 is a proximally oriented view of the bidirectional snare device presented in FIG. 40;

FIG. 43 is an enlarged partial section view of the bidirectional snare device presented in FIG. 42;

FIG. 47A is a perspective view of a single suture and crimped sleeve as applied in the intended field of use as a coaxial mechanical fastener;

FIG. 47B is a perspective view of the coaxial fastener first shown in FIG. 47A with the crimped sleeve removed for clarity;

FIG. 48A is a perspective view of two separate sutures and crimped sleeve as applied in the intended field of use as a coaxial mechanical fastener;

FIG. 48B is a perspective view of the coaxial fastener first shown in FIG. 48A with the crimped sleeve removed for clarity;

FIG. 49A is a perspective view of three separate sutures and crimped sleeve as applied in the intended field of use as a coaxial mechanical fastener;

FIG. 49B is a perspective view of the coaxial fastener first shown in FIG. 49A with the crimped sleeve removed for clarity;

FIG. 50 is a frontal perspective view of the deployment device of FIG. 5 with an attachment slotted suture securing reel in the intended field of use;

FIG. 51 is an exploded perspective view of the slotted suture securing reel of FIG. 50;

DETAILED DESCRIPTION OF THE INVENTION

Figure 5C:
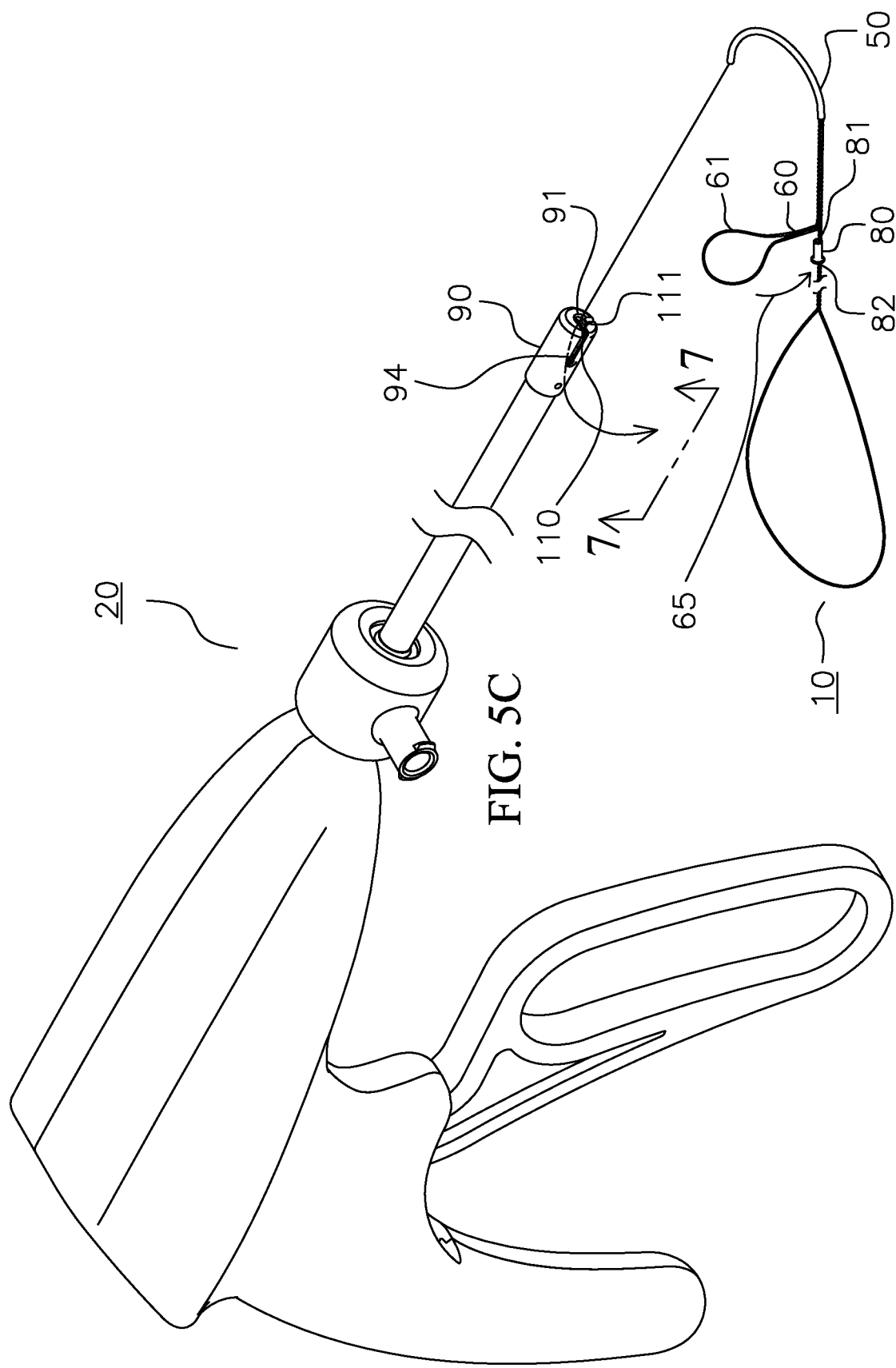
FIG. 5C is a distally oriented perspective view of the bidirectional snare device of FIG. 1 in an alternative installation configuration for use in a corresponding deployment device when applied to its field of use.

Referring to FIGS. 1 through 4, a bidirectional snare device 10 is shown. FIG. 1 is a distally oriented perspective view of the bidirectional snare device 10. The bidirectional snare device 10 consists of a curved handle 50 which fixedly holds a short wire snare 60 and a long wire snare 70 within a receiving bore 51. The curved handle 50 is typically comprised of a medical-grade stainless steel and formed in such a manner to allow for manipulation by the user. The short wire snare 60 and long wire snare 70 are also made from medical-grade stainless steel, but in small diameter wire form. The short wire snare 60 and long wire snare 70 pass through a wire bore 81 of a malleable sleeve 80. The sleeve is typically manufactured form a nonreactive, biocompatible material such as titanium and is fashioned that the distal end has an enlarged flange 82 connected to a body 83 of a slightly smaller diameter. The long wire snare 70 is formed by bending a length of wire 72 into a loop 71 with a twisted end 73. The short wire snare 60 is formed by bending a substantially shorter length of wire 62 into a loop 61 with a twisted end 63. The twisted end 73 of the long wire snare 70 is passed directly through the wire bore 81 of the sleeve 80 positioning the loop 71 distally from the flange 82. The twisted end 63 of the short wire loop 60 is passed through the wire bore 81 of the sleeve 80 from the opposite direction than the long wire snare 70. Twisted end 63 and twisted end 73 are inserted into the receiving bore 51 and fixedly attached via mechanical means such as welding or crimping.

FIG. 2 is an enlarged partial cross-sectional perspective view of the bidirectional snare device 10 of FIG. 1 showing the twisted end 73 of the long wire snare 70, clearly shown in FIG. 1, adjacent to the untwisted pair 64 of the short wire snare 60 passing through the wire bore 81 of sleeve 80.

FIG. 3 is a proximally oriented perspective view of the bidirectional snare device 10 show in in FIG. 1. Again, the twisted end 73 of the long wire snare 70 passes through the wire bore 81 of the sleeve 80 with the loop 71 positioned distal to the flange 82. The short wire snare 60 is passed through the sleeve 80 such that the loop 61 is proximal to the flange 82 and the untwisted pair 64 pass through the wire bore 81 of the sleeve 80 and wraps around the body 83 and the twisted end 63 is positioned parallel to and coincident with the twisted end 73 of the long wire snare 70. Twisted end 73 and twisted end 63 are fixedly attached to curved handle 50.

FIG. 4 is an enlarged partial cross-sectional perspective view of the bidirectional snare device 10 of FIG. 3 showing the twisted end 73 of the long wire snare 70, clearly shown in FIG. 3, adjacent to the untwisted pair 64 of the short wire snare 60 passing through the wire bore 81 of sleeve 80.

FIG. 5 is a distally oriented perspective view of the bidirectional snare device 10 and a deployment device 20. The curved handle 50 of the bidirectional snare device 10 is inserted through a distal opening 91 and exits an exit port 92 (best illustrated in FIG. 5B) in a distal tip 90 until the flange 82 of the sleeve 80 rests firmly against a frontal face 111 of a hammer anvil 110 within the distal tip 90.

FIG. 5A is an enlarged perspective view of the distal end of the deployment device 20 of FIG. 5 with the installed bidirectional snare device 10 of FIG. 1. The twisted end 73 and twisted end 63 of the long wire snare 70 and the short wire snare 60, respectively exit the distal tip 90 through the exit port 92 (best shown in FIG. 5B). The remaining twisted end 73 exits the distal opening 91, positioning loop 71 distal to the distal tip 90. The loop 61 of the short wire snare 60 and the untwisted pair 64 exit the distal tip 90 through a loop channel 94. The sleeve 80 is shown with the flange 82 seated against the frontal face 111 of the hammer anvil 110 within the distal tip 90.

FIG. 5B is an enlarged perspective view of the deployment device 20 along lines 5B-5B of FIG. 5 with the installed bidirectional snare device 10 of FIG. 1. The twisted end 73 and twisted end 63 of the long wire snare 70 and the short wire snare 60, respectively exit the distal tip 90 through the exit port 92. The loop 71 of the long wire snare 70 is positioned distal to the tip 90. The loop 61 of the short wire snare 60 and the untwisted pair 64 (not shown) exit the distal tip 90 through a loop channel 94.

FIG. 5C is a distally oriented perspective view of the bidirectional snare device 10 and a deployment device 20 in an alternate assembly configuration. The small loop 61 of the short wire snare 60 is first routed in direction 65 through the exit port 92 over a projecting suture elevator 120, out of the entry port 96, through the trough 95 (all part of the distal tip 90 and best shown in FIG. 7). The small loop 61 of the short wire snare is then inserted into the flange 82 and through the wire bore 81 of the sleeve 80 and finally out through the loop channel 94 of the distal tip 90. The curved handle 50 of the bidirectional snare device 10 is inserted through a distal opening 91 and exits the exit port 92 (best illustrated in FIG. 7) in the distal tip 90 until the flange 82 of the sleeve 80 rests firmly against a frontal face 111 of a hammer anvil 110 within the distal tip 90.

FIG. 6 is an enlarged perspective view of the distal end of the deployment device 20 of FIG. 5C with the installed bidirectional snare device 10 of FIG. 1. The twisted end 73 and twisted end 63 of the long wire snare 70 and the short wire snare 60, respectively exit the distal tip 90 through the exit port 92 (also best shown in FIG. 7). The remaining twisted end 73 exits the distal opening 91, positioning loop 71 distal to the tip 90. The loop 61 of the short wire snare 60 exits the distal tip 90 through a loop channel 94 and the untwisted pair 64 lay within a trough 95 (also better shown in FIG. 7) in the distal tip 90. The sleeve 80 is shown with the flange 82 seated against the frontal face 111 of the hammer anvil 110 within the distal tip 90.

FIG. 7 is an enlarged perspective view of the deployment device 20 along lines 7-7 of FIG. 5C with the installed bidirectional snare device 10 of FIG. 1. The twisted end 73 and twisted end 63 of the long wire snare 70 and the short wire snare 60, respectively, exit the distal tip 90 through the exit port 92. The loop 71 of the long wire snare 70 is positioned distal to the tip 90. The loop 61 of the short wire snare 60 exits the distal tip 90 through a loop channel 94 and the untwisted pair 64 lay within a trough 95 in the distal tip 90.

FIG. 8 is a proximally oriented perspective view of the bidirectional snare device 10 and a deployment device 20. The curved handle 50 of the bidirectional snare device 10 exits the distal tip 90 and remains in line with a shaft tube 230 of deployment device 20.

FIG. 9 is an enlarged perspective view of the distal end of the deployment device 20 of FIG. 8 showing the curved handle 50 and twisted end 73 of the long wire snare 70 and short wire snare 60, respectively, running parallel to the axis of the shaft tube 230 of the deployment device 20. The loop 71 of the long wire snare 70 is shown positioned distal to the distal tip 90 while the loop 61 of the short wire snare 60 is shown exiting the loop channel 94 of the distal tip 90.

FIG. 10 is a partial orthogonal section view of the deployment device 20 and bidirectional snare device 10 along lines 10-10 of FIG. 8. The loop 61 of the short wire snare 60 exists the loop channel 94 of the distal tip 90 while the twisted end 73 of the long wire snare 70 and twisted end 63 of the short wire snare 60, respectively, exit the exit port 92 of the distal tip 90. The flange 82 of the sleeve 80 rests flush with the frontal face 111 of the hammer anvil 110.

FIG. 11 is a partial orthogonal section view of the deployment device 20 and bidirectional snare device 10 along lines 11-11 of FIG. 9 wherein the flange 82 of the sleeve 80 rests against the frontal face 111 of the hammer anvil 110, The untwisted pair 64 of the short wire snare 60 rests within the trough 95 of the distal tip 90 and reenters the distal tip 90 through an entry port 96, routed over a suture elevator 120 and through the exit port 92 parallel to and coincident with the twisted end 73 of the long wire snare 70.

Referring to FIGS. 12 through 19, the method of loading suture tails 130 of suture 133 from a leaflet 150 (shown in FIG. 36) and suture tails 140 of suture 146 from a papillary muscle 160 (also shown in FIG. 36) into the bidirectional snare device 10 and the deployment device 20.

FIG. 12 is a partial distally oriented rear perspective view of the deployment device 20 with installed bidirectional snare device of FIG. 8 showing suture tails 130 of suture 133 placed into the loop 61 of the short wire snare 60 of the bidirectional snare device 10.

FIG. 13 is a progression of FIG. 12 where the curved handle 50 of the bidirectional snare device 10 is pulled in the direction 52 relative to the deployment of device 20. The loop 61 from FIG. 12 has retracted into the distal tip 90 pulling the suture tails 130 of suture 133 in direction 131 and further into the distal tip 90 while the loop 71 of the long wire snare 70 of the bidirectional snare device 10 progresses in direction 74 towards the distal tip 90.

FIG. 14 is a progression of FIG. 13 where the curved handle 50 of the bidirectional snare device 10 is pulled further in the direction 52 relative to the deployment device 20. The loop 61 has collapsed and fully withdrawn from the distal tip 90, pulling the suture tails 130 of suture 133 in direction 132 fully through and exiting the distal tip 90. The loop 71 of the long wire snare 70 of the bidirectional snare device 10 progresses further in the direction 74 towards the distal tip 90.

FIG. 15 is a partial distally oriented rear perspective view of the deployment device with installed bidirectional snare device of FIG. 8 showing suture tails 140 of suture 146 placed into the loop 71 of the long wire snare 70 of the bidirectional snare device 10.

FIG. 16 is a progression of FIG. 15 where the curved handle 50 of the bidirectional snare device 10 is pulled in the direction 52 relative to the deployment device 20. The loop 71 of the long wire snare 70 of the bidirectional snare device 10 further retracts in the direction 74 into the distal tip 90 pulling the suture tails 140 of suture 146 toward the distal tip 90.

FIG. 17 is a progression of FIG. 16 where the curved handle 50 of the bidirectional snare device 10 is pulled further in the direction 52 relative to the deployment device 20. The loop 71 of the long wire snare 70 of the bidirectional snare device 10 has progressed further in the direction 74 and has collapsed and withdrawn from the distal tip 90, pulling the suture tails 140 of suture 146 in direction 141 fully through and exiting the distal tip 90.

FIG. 18 is a final progression of FIG. 17 where the suture tails 140 of suture 146 have been pulled in direction 142 and completely through the distal tip 90. The bidirectional snare device 10 (last shown in FIG. 17) is disposed.

FIG. 19 is a partial distally oriented rear perspective view of the deployment device 20 in FIG. 8 showing suture tails 130 of suture 133 and suture tails 140 of suture 146 being tensioned in direction 143 as the deployment device 20 is extended in direction 145 to place the distal tip 90 on the desired deployment site.

FIG. 20 is a perspective view of a coaxial mechanical fastener 30 with suture 133 attached to a leaflet 150 and the suture 146 attached to a papillary muscle 160 a now crimped sleeve 80 retains both suture 133 and suture 146 such that the suture tails 130 exit from the flange 82 of the sleeve 80 and the suture tails 140 exit from the body 83 of the sleeve 80.

Figure 21:
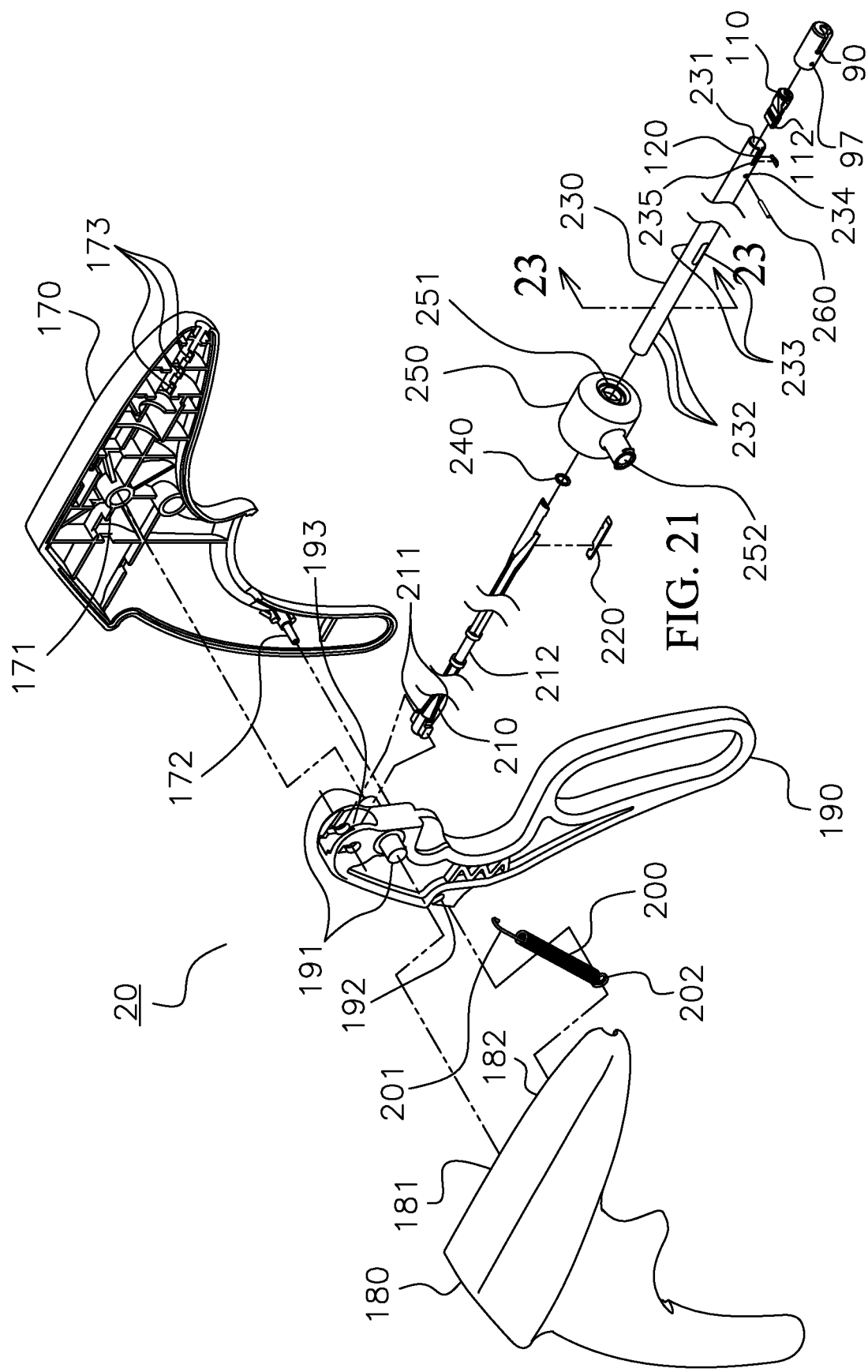
FIG. 21 is a distally oriented exploded perspective view of the deployment device of FIG. 5C.

FIG. 21 is an exploded perspective view of the deployment device 20. The deployment device 20 comprises a left handle 170, right handle 180, and a lever 190 all of which are suitably manufactured from a medical grade plastic via an injection molding process. The lever 190 is constrained by and pivots about posts 191 that are circumferentially disposed within pivot bore 171 of the left handle 170 and a similarly defined pivot bore 181 (not shown) within the right handle 180. An extension spring 200, typically made from a biocompatible material such as stainless steel, provides a preload to the lever 190 by attaching to a spring tab 192 on the lever 190 via a hook 201 and attaching to a post 172 in the left handle 170 via a loop 202. A wedge tip 210 is retained in a pocket 193 of the lever 190 by rotational posts 211. The wedge tip is made, preferably, from a medical grade plastic via the injection molding process. A cutter blade 220, made from a medical grade metal such as stainless steel is attached to the wedge tip 210 and retained and constrained by the geometry of the wedge tip 210 and an internal bore 231 of a shaft tube 230. The shaft tube 230, preferably made from stainless steel, is constrained by mating slots 232 in the shaft tube 230 and fingers 173 and fingers 182 (not shown) within the left handle 170 and the right handle 180, respectively. A fluid-tight seal is maintained at the proximal end of the shaft tube 230 and wedge tip 210 by the installation of an o-ring 240 over a groove 212 of the wedge tip 210. A fluid housing 250, made from plastic, is slid over the shaft tube 230 through a shaft bore 251 such that a communication bore 252 aligns with fluid channels 233 in the shaft tube 230. The hammer anvil 110, also manufactured from a medical grade metal such as stainless steel or the like, is secured within the distal end of the shaft tube 230 by press fitting a pin 260 through pin hole 97 in the distal tip 90 and pin hole 234 in the shaft tube 230 and through a pin channel 112 in the hammer anvil 110. The suture elevator 120, comprised of a medical grade stainless steel, is installed within the shaft tube 230 by press fitting into an elevator slot 235.

Figure 22:
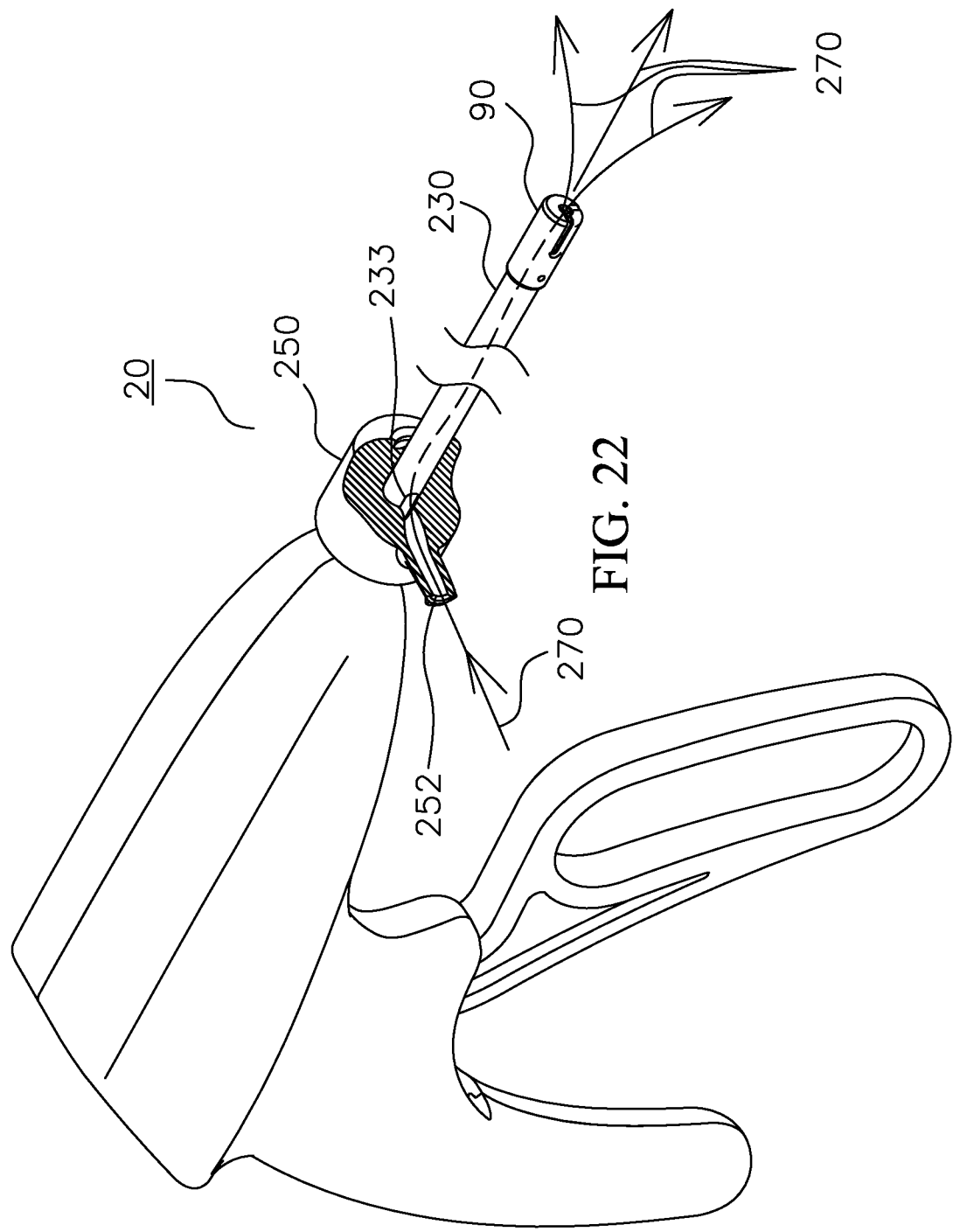
FIG. 22 is a distally oriented, partially sectioned perspective view of the deployment device of FIG. 5C showing the introduction of fluid in the intended field of use.

FIG. 22 is a distally oriented partially sectioned perspective view of the deployment device 20 of FIG. 5 showing the introduction of fluid 270 through the communication bore 252 of the fluid housing 250 and subsequently through the fluid channels 233 in the shaft tube 230. Fluid 270 flows through the shaft tube 230 and out of the distal tip 90 to provide infusion.

Figure 23:
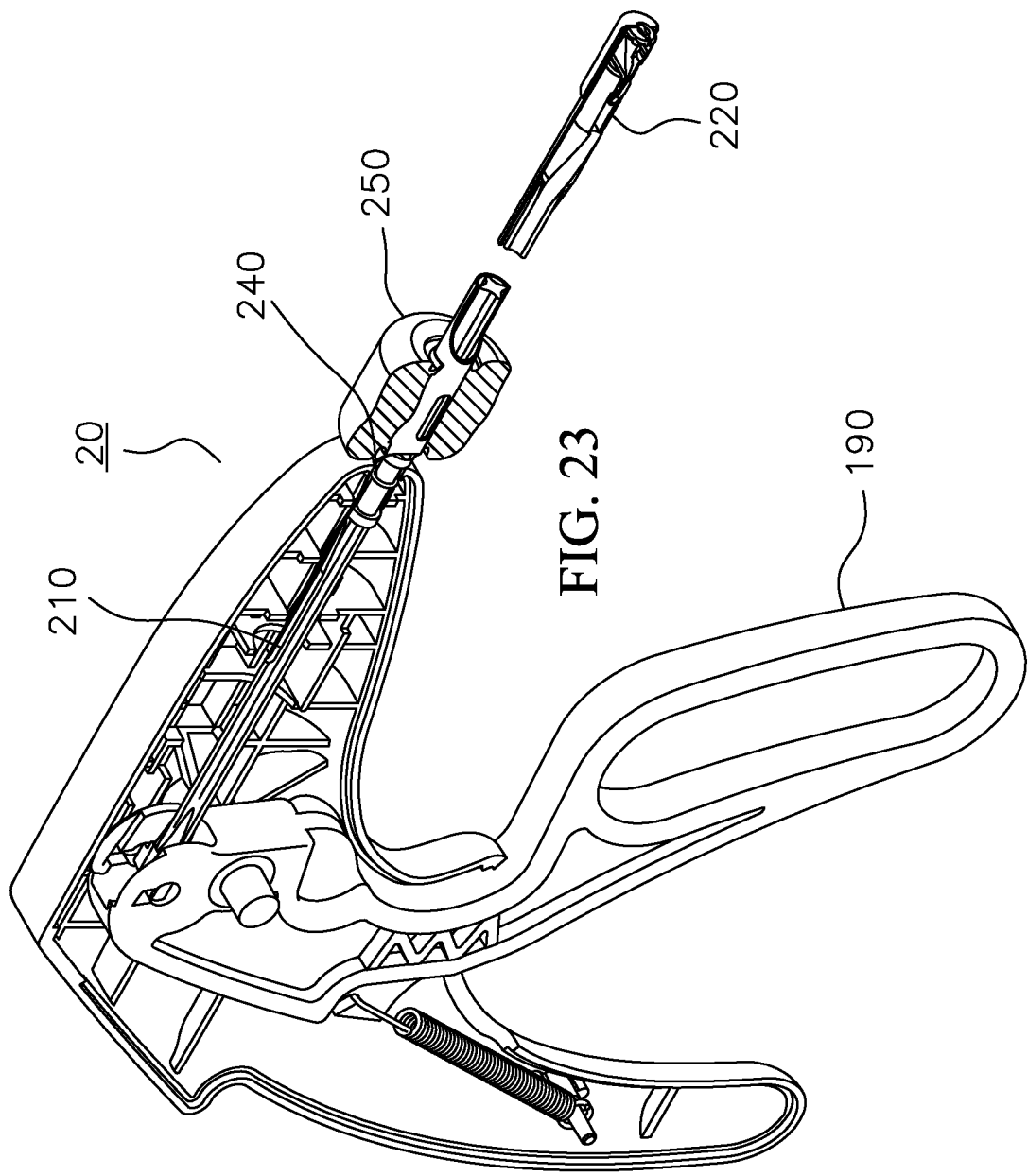
FIG. 23 is a distally oriented, partial section view along lines 23-23 in FIG. 21.

FIG. 23 is a distally oriented, partial section view of the deployment device 20 along lines 23-23 in FIG. 21 wherein the lever 190 is fully extended in its natural position, the wedge tip 210 and attached cutter blade 220 are refracted with the o-ring 240 providing a seal during fluid communication through the fluid housing 250. The bidirectional snare device 10 is not shown for clarity.

Figure 24:
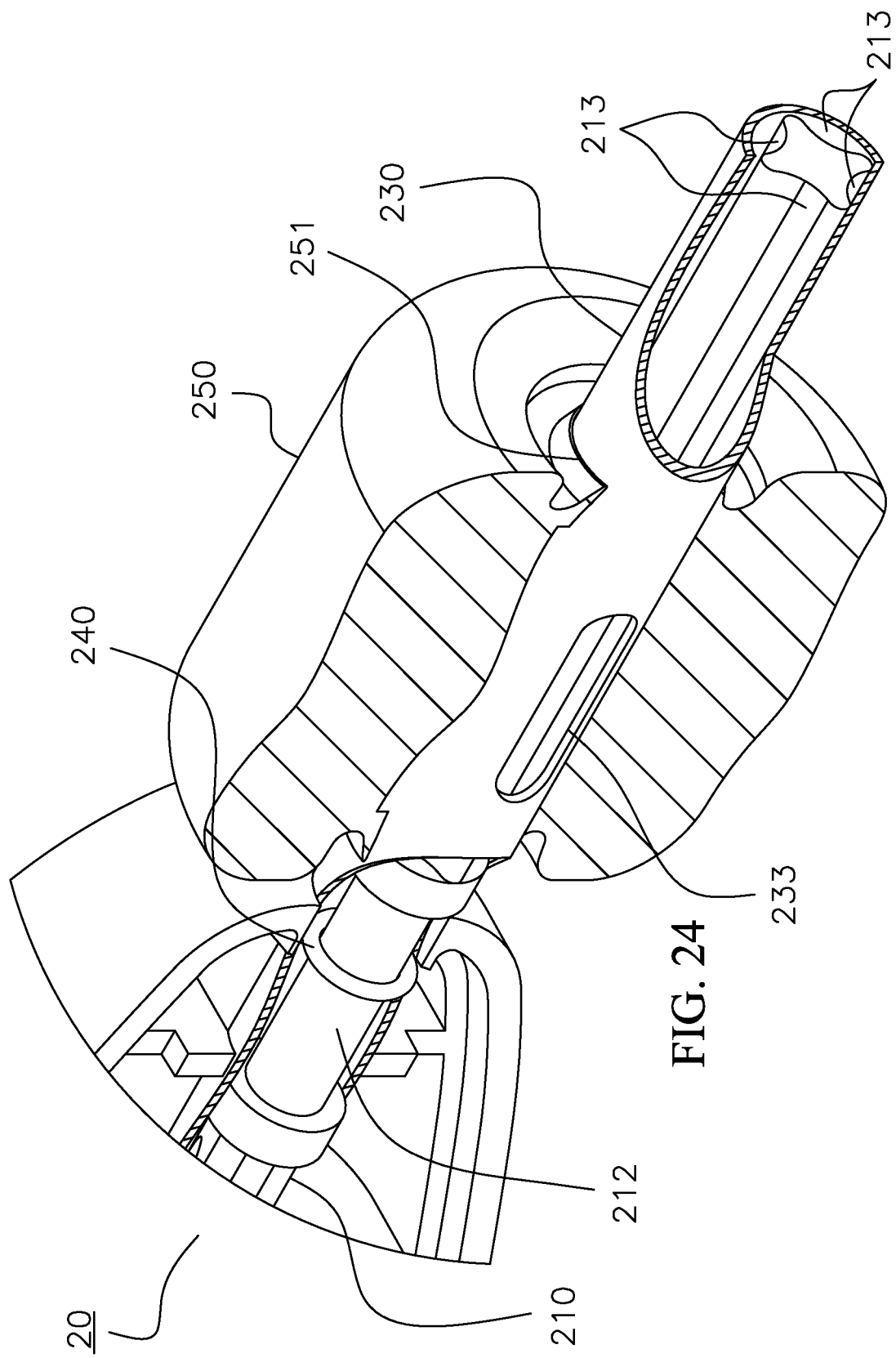
FIG. 24 is an enlarged perspective view of the middle portion of the deployment device from FIG. 23.

FIG. 24 is an enlarged partial view of FIG. 23 illustrating the position of the o-ring 240 on the groove 212 of the wedge tip 210 within the shaft tube 230. The fluid housing 250 provides a fluid tight seal via the compression fit of shaft bore 251 on the shaft tube 230. Fluid passes through the fluid housing 250 into the shaft tube 230 by way of fluid channels 233 and through the shaft tube 230 over the wedge tip 210 by way of fluid troughs 213.

Figure 25:
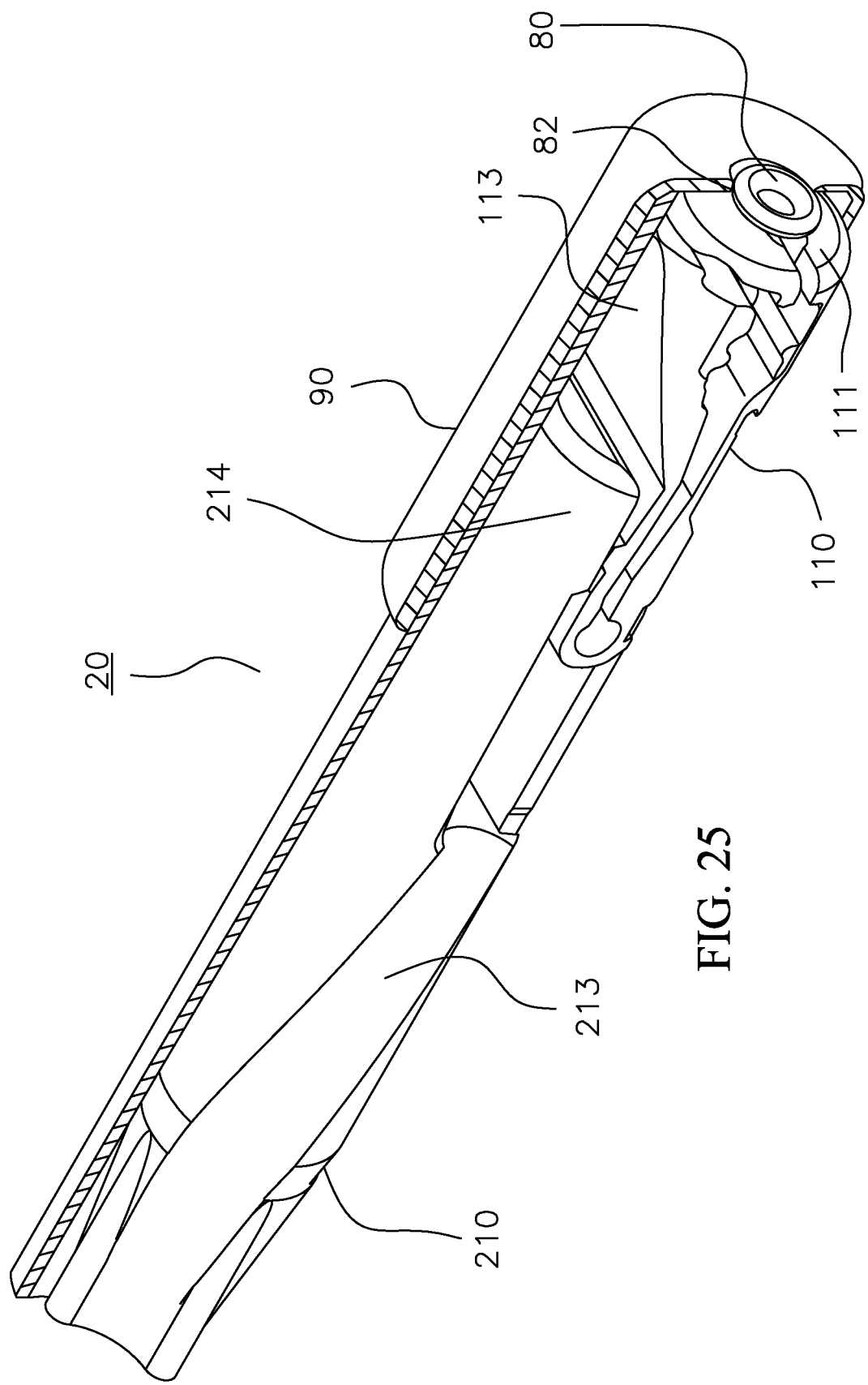
FIG. 25 is an enlarged perspective view of the distal portion of the deployment device from FIG. 23.

FIG. 25 is an enlarged partial view of FIG. 23 illustrating the position of the wedge tip 210 in relation to the hammer anvil 110. The fluid troughs 213 of the wedge tip 210 communicate fluid to the distal tip 90. An arm 214 of wedge tip 210 is proximal to and not engaging a ramp 113 of the hammer anvil 110. The sleeve 80 is shown with the flange 82 resting against the frontal face 111 of the hammer anvil 110.

Figure 26:
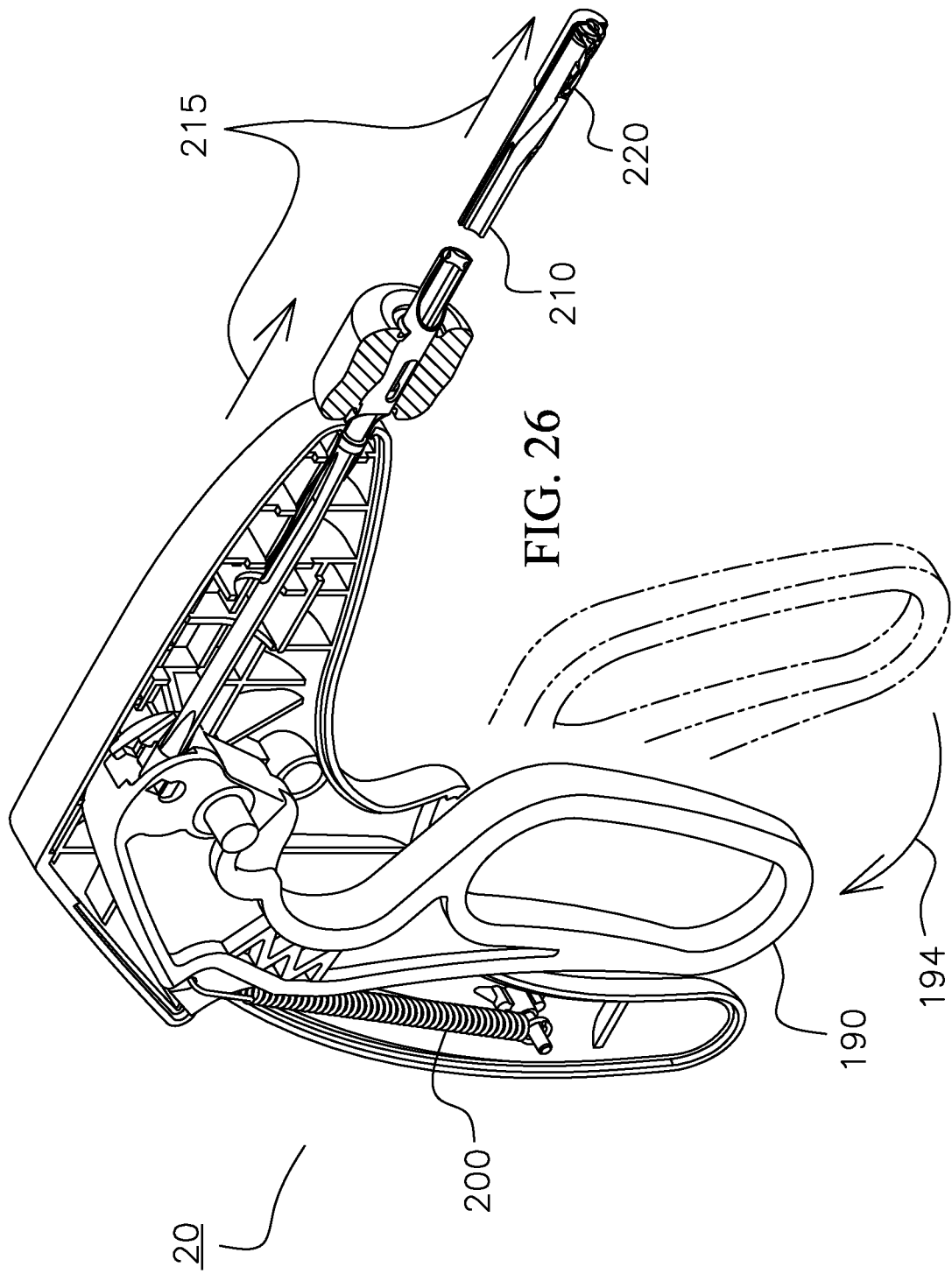
FIG. 26 is an additional view of the device shown in FIG. 23 actuated as in the field of use.

FIG. 26 is a distally oriented, partial section view of the deployment device 20 along lines 23-23 in FIG. 21 wherein the lever 190 is fully retracted in direction 194, extending the extension spring 200 and driving the wedge tip 210 and cutter blade 220 in direction 215. The bidirectional snare device 10 is not shown for clarity.

Figure 27:
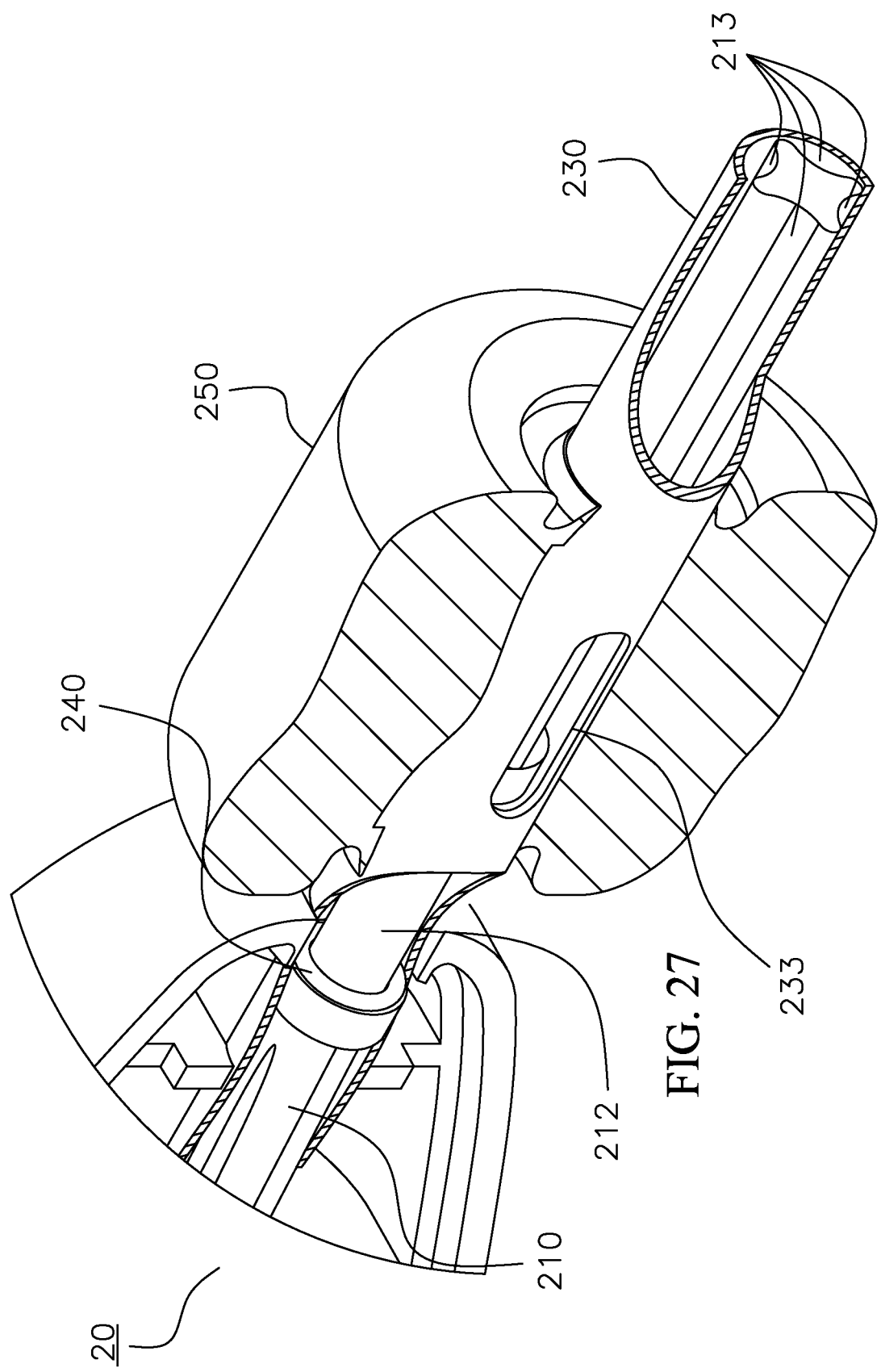
FIG. 27 is an enlarged perspective view of the middle portion of the deployment device from FIG. 26.

FIG. 27 is an enlarged partial view of FIG. 26 illustrating the position of the o-ring 240 on the now advanced groove 212 of the wedge tip 210 within the shaft tube 230. Fluid is allowed to communicate through the shaft tube 230 by way of the fluid housing 250 and coinciding fluid channels 233 of the shaft tube 230 and over the fluid troughs 213 of wedge tip 210.

Figure 28:
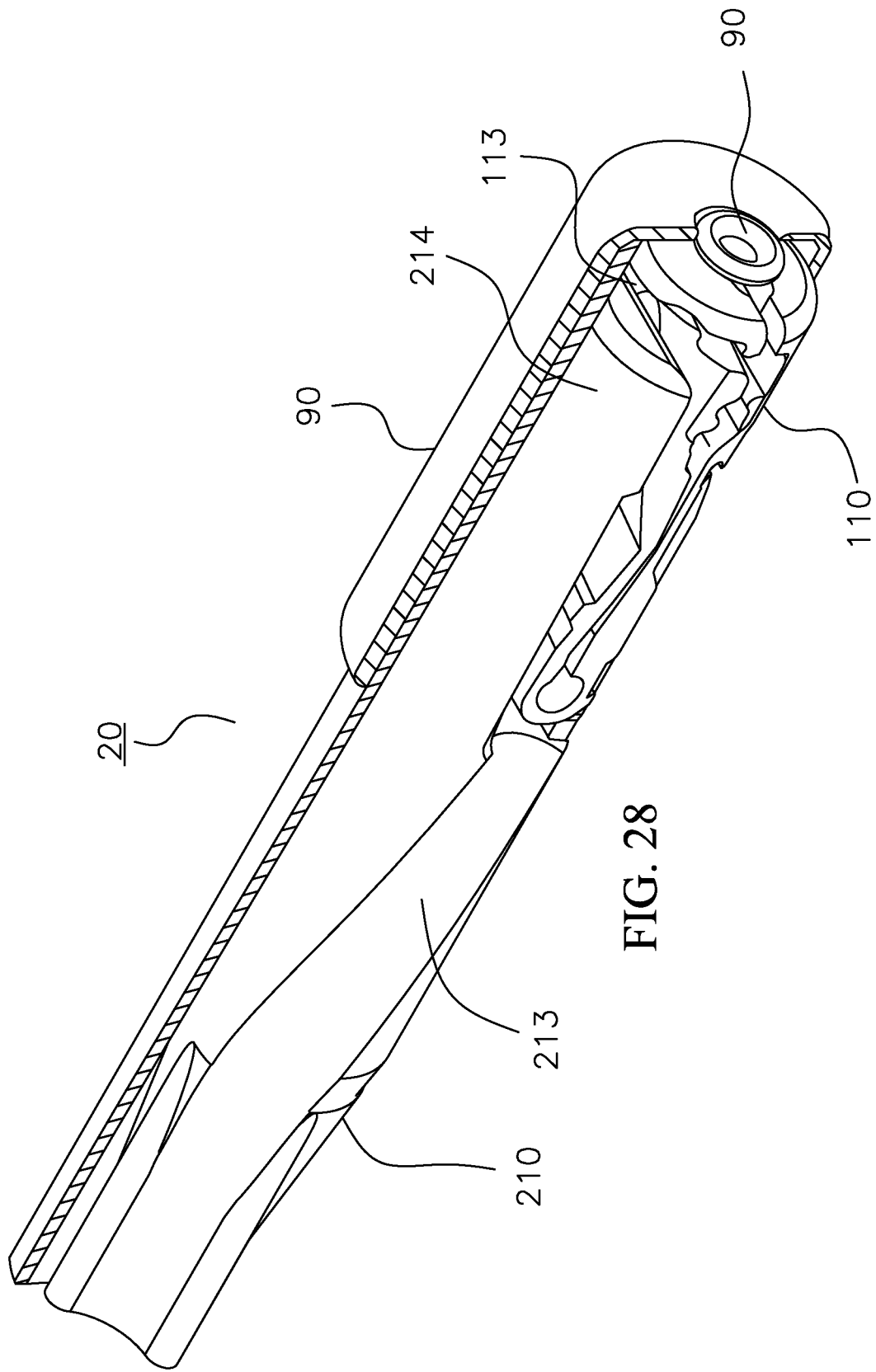
FIG. 28 is an enlarged perspective view of the distal portion of the deployment device from FIG. 26 illustrating the crimping of a sleeve.

FIG. 28 is an enlarged partial view of FIG. 26 illustrating the position of the wedge tip 210 in relation to the hammer anvil 110. The fluid troughs 213 of the wedge tip 210 communicate fluid to the distal tip 90. The arm 214 of the wedge tip 210 is now engaging the ramp 113 of the hammer anvil 110 and causing the hammer anvil 110 to compress the sleeve 80.

FIG. 28A is an orthogonal section view along view lines 28-28 of FIG. 28 illustrating the advanced wedge tip 210 compressing the hammer anvil 110 and sleeve 80 and the also advanced cutter blade 220 impacting the suture elevator 120 and trimming suture tails 130 and suture tails 140.

FIG. 28B is an alternate enlarged partial section view of FIG. 28 again illustrating the advanced wedge tip 210 compressing the hammer anvil 110 and sleeve 80 and the also advanced cutter blade 220 impacting the suture elevator 120 and trimming suture tails 130 and suture tails 140.

FIG. 29 is an enlarged perspective view of the sleeve 80 compressed by the actions detailed in FIG. 28. The body 83 of sleeve 80 is compressed, but the flange 82 is intact.

FIG. 30 shows a schematic illustration of the human heart 40 sectioned to remove the front from the left side of the heart. This heart 40 is shown during diastole which is the filling phase during the cardiac cycle. The right side is not highlighted in this illustration. The left atrium 300 receives blood returning from the lungs through the pulmonary veins 301 and 302. Two pulmonary veins generally enter to the left atrium 300 on the patient's right side 300A and two more on the patient's left atrial side 300B. Note the four open arrows 303 coming from the pulmonary veins 301 and 302 illustrating the return of blood flow to the left atrium 300. During this phase of the cardiac cycle, the anterior leaflet 304 of the mitral valve 305 and the posterior leaflet 306 of the mitral valve 305 are open to permit the blood returning to the atrium 300 to pass into the left ventricle 307. Note that the chordae tendineae 308 is shown passing from the anterior leaflet 304 of the mitral valve 305 to a papillary muscle 309 in the left ventricle 307. Note that a second chordae tendineae 310 is shown here passing from the posterior leaflet 306 to another papillary muscle 311. The thin black arrows 312 indicate the opening of the anterior and posterior mitral valve leaflets, 304 and 306. The aortic valve 314 is shown in the closed position as it is during diastole due to back pressure from blood in the ascending aorta 315. For purposes of clarity, this illustration does not show the right atrium or the right ventricle.

FIG. 31 illustrates the heart 40 now in the contraction phase, systole, of the cardiac cycle. The cardiac walls 316 and septum 317 thicken as the ventricular chamber 318 contracts. The thin black arrows 312 and 313 illustrate that the pressure built up in the left ventricle 307 causes both the anterior mitral leaflet 304 and posterior mitral leaflet 306 to come together and seal at what is called the coaptation zone 319. The four open arrows illustrate blood leaving the left ventricle and passing through the now open aortic valve 314.

Figure 32:
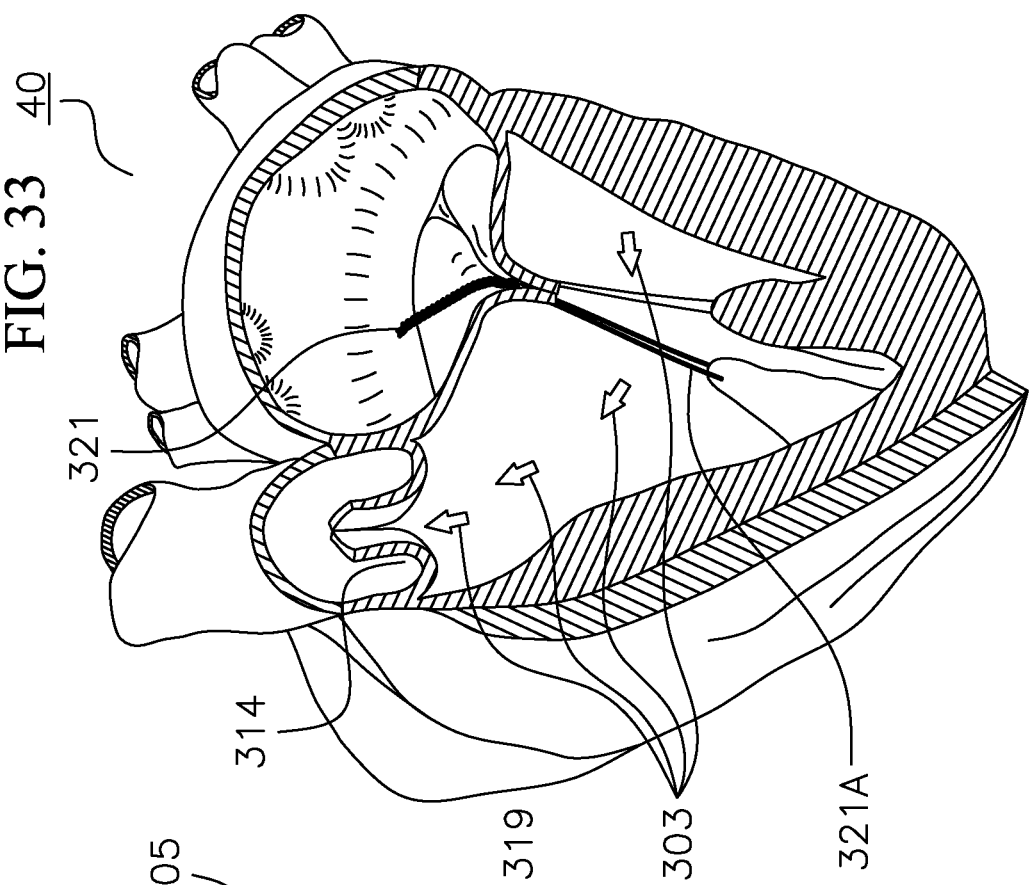
FIG. 32 is a partial section schematic view illustrating the human heart in systole with the left front side removed highlighting a ruptured chordae tendineae on the anterior leaflet of the mitral valve.

FIG. 32 is similar to FIG. 31 with the schematic heart 40 in systole. However, here the chordae tendineae 308 in FIG. 30 which should be in continuity between the papillary muscle 309 and the anterior leaflet 304 of the mitral valve 305 has been disrupted. This disrupted chordae tendineae 320 is shown partially attached to the papillary muscle 309 and partially attached 320 to the anterior leaflet 304. The coaptation zone 319 between the anterior leaflet 304 and the posterior leaflet 306 is disrupted allowing blood to pass back into the left atrium 300 instead of being blocked by the coapted mitral valve 305. This passing of blood back into the right atrium is called regurgitation, and the movement of the anterior leaflet into the left atrium is called prolapse.

Figure 33:
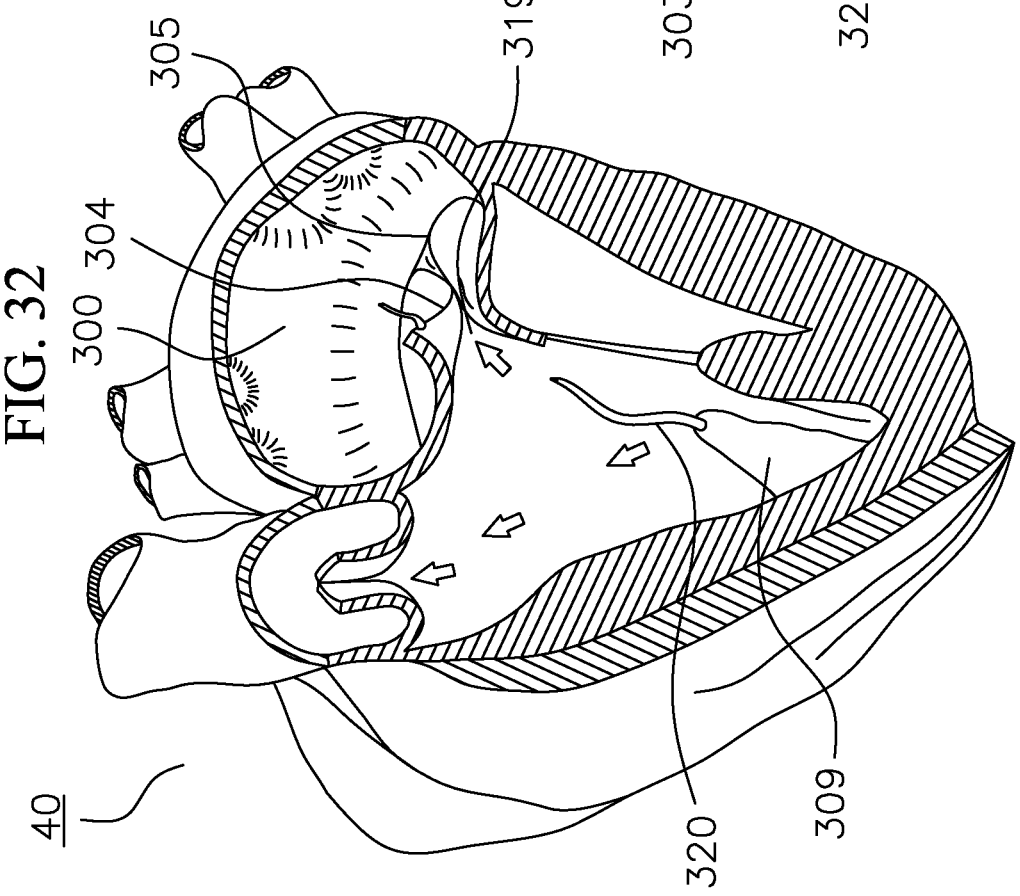
FIG. 33 is a partial section schematic view illustrating the human heart in systole with the left front side removed highlighting a correct length hand-tied replacement suture from a papillary muscle to the anterior leaflet of the mitral valve.

FIG. 33 shows a proper length suture hand-tied replacement 321 for a disrupted chordae tendineae, which is not shown here due to its surgical removal. The open arrows 303 indicating blood show that the blood again passes only towards the now open aortic valve 314.

FIG. 34 is similar to the illustration of FIG. 33 however in FIG. 34 the hand-tied suture replacement 321 of suture 321A (for the anterior leaflet 304 disrupted chordae tendineae 308 as shown in FIG. 32) is tied too long so that the anterior leaflet 304 can prolapse into the left atrium 300 thereby rendering the coaptation zone 319 dysfunctional. One open arrow illustrates the passage of blood regurgitating back into the left atrium 300 due to inaccurate knotting of the chordae tendineae replacement suture 321.

FIG. 35 is like FIGS. 33 and 34 however now the chordae tendineae replacement suture 321 is too short. By tying the replacement suture 321 of suture 321A too short, the coaptation zone 319 of the mitral valve 305 is rendered open. The inappropriate coaptation of the anterior leaflet 304 leaves a space between the anterior leaflet 304 and the posterior leaflet 306 through which blood can pass as illustrated with the open arrow 323.

FIG. 36 shows the tip of the deployment device 20 of the present invention passing into the schematic left atrium 300 of the human heart 40. Note there are two different loops of suture, 324 and 325, one coming from the papillary muscle 309 and another coming from the anterior leaflet 304 whose chordae tendineae has been removed.

FIG. 37 shows similar illustration as FIG. 36 except now the deployment device 20 has passed completely down onto the papillary muscle 309 in the left ventricle 307. The suture 324 going from papillary muscle 309 and through the coaxial mechanical fastener 30 is drawn tight. However the suture 325 going to the anterior leaflet 304 has yet to be drawn down into the proper coaptation alignment.

FIG. 38 shows the schematic heart 40 with the deployment device 20 in place on the papillary muscle 309 and now also infusing pressurized saline 326 into the left ventricle 307 to push upon the inside surfaces of both the mitral leaflets 304 and 306, as indicated by the thin black arrows 313. By drawing the suture 325 from the anterior leaflet 304 in, the anterior leaflet 304 is pulled down into position in the appropriate zone for coaptation. When the suture length is properly set, the lever 190 (not shown) of the deployment device 20 is squeezed, crimping the coaxial fastener 30 and simultaneously cutting away all redundant suture 324 and 325 through the suture hole (not shown).

FIG. 39 shows the coaxial fastener 30 in place anchoring the suture 325 coming from the anterior leaflet 304 to the papillary muscle 309. The double headed arrow 327 indicates the direction of the tension from the papillary muscle 309 up to the anterior leaflet 304. Note that the coaptation zones 319 are completely in contact and the inner surfaces of both the anterior and posterior mitral leaflets 304 and 306 are parallel and aligned.

FIG. 40 is a distally oriented perspective view of an additional embodiment of a bidirectional snare device 280.

The bidirectional snare device 280 is formed by first forming a small loop 284 and routing the wire pair 288 through the body 83 of the sleeve 80. Looping the wire pair 288 around the flange 82 of the sleeve 80. While maintaining a small loop 284, arrange the wire pair 288 so that one end is substantially longer than the other and create a twisted portion 285 of about ½ inch in length approximately 2 inches from the small loop 284. Route the remaining long end of wire 283 through the body 83 of the sleeve 80 and form a large loop 282 again feeding the end of the wire 283 back through the flange 82 of the sleeve 80. Twist a portion 286 of about 3-4 inches in length until it meets the twisted portion 285. Finally taking the remaining free ends of wire 283, create a twisted pair end 287 and secure within the receiving bore 51 of the curved handle 50.

FIG. 41 is an enlarged partial cross-sectional perspective view of the bidirectional snare device 280 of FIG. 40 showing the twisted portion 286 and the wire pair 288 adjacent to each other inside of the wire bore 81 of sleeve 80.

FIG. 42 is a proximally oriented perspective view of the bidirectional snare device 280 shown in FIG. 40. The large loop 282 is distal from the flange 82 of the sleeve 80 and the small loop 284 is proximal to the body 83 of the sleeve 80.

FIG. 43 is an enlarged partial cross-sectional perspective view of the bidirectional snare device 280 of FIG. 42 again showing the twisted portion 286 and the wire pair 288 adjacent to each other inside of the wire bore 81 of sleeve 80.

Figure 44:
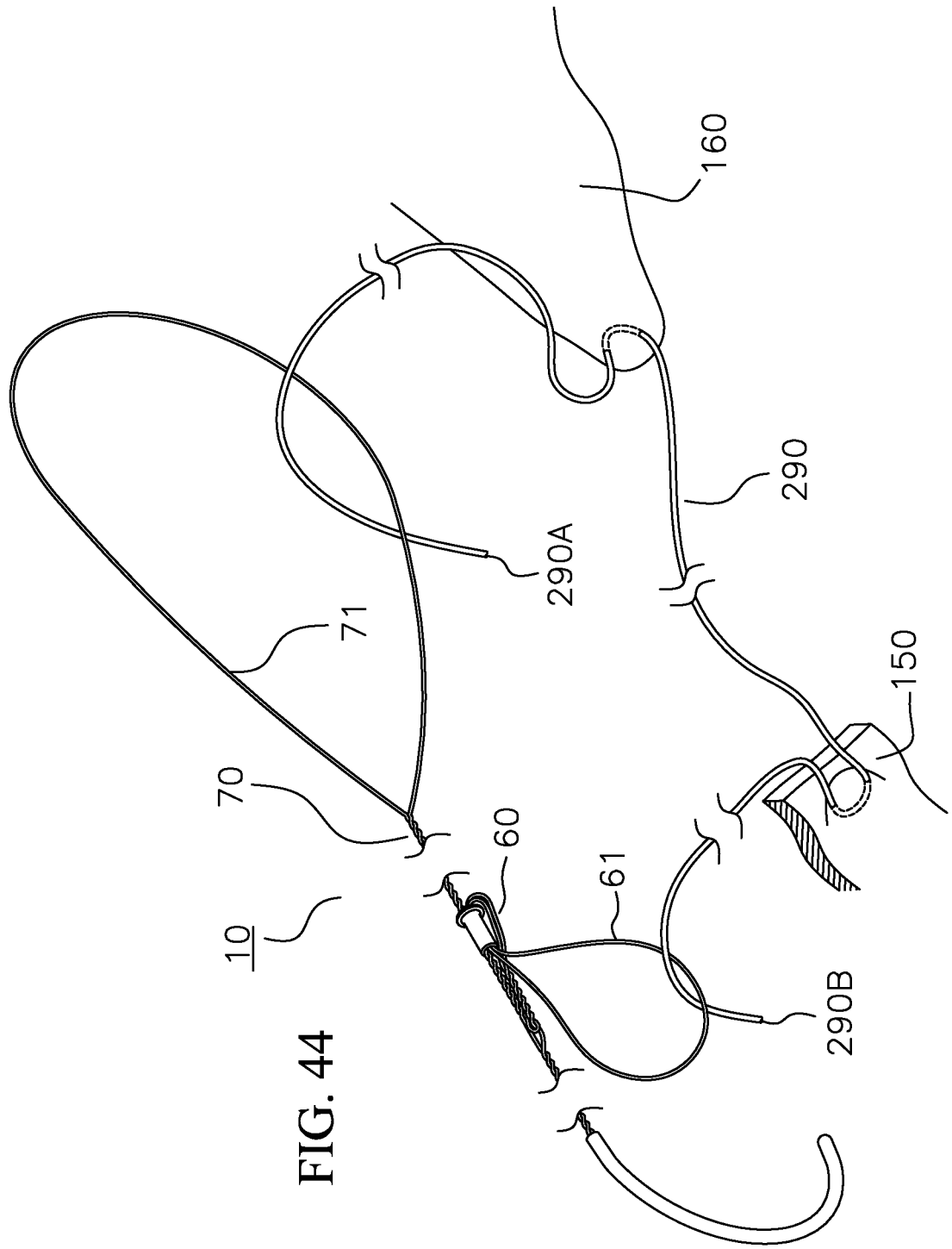
FIG. 44 is a perspective view illustrating the application of a single emplaced suture with the apparatus first shown in FIG. 1.
Figure 45:
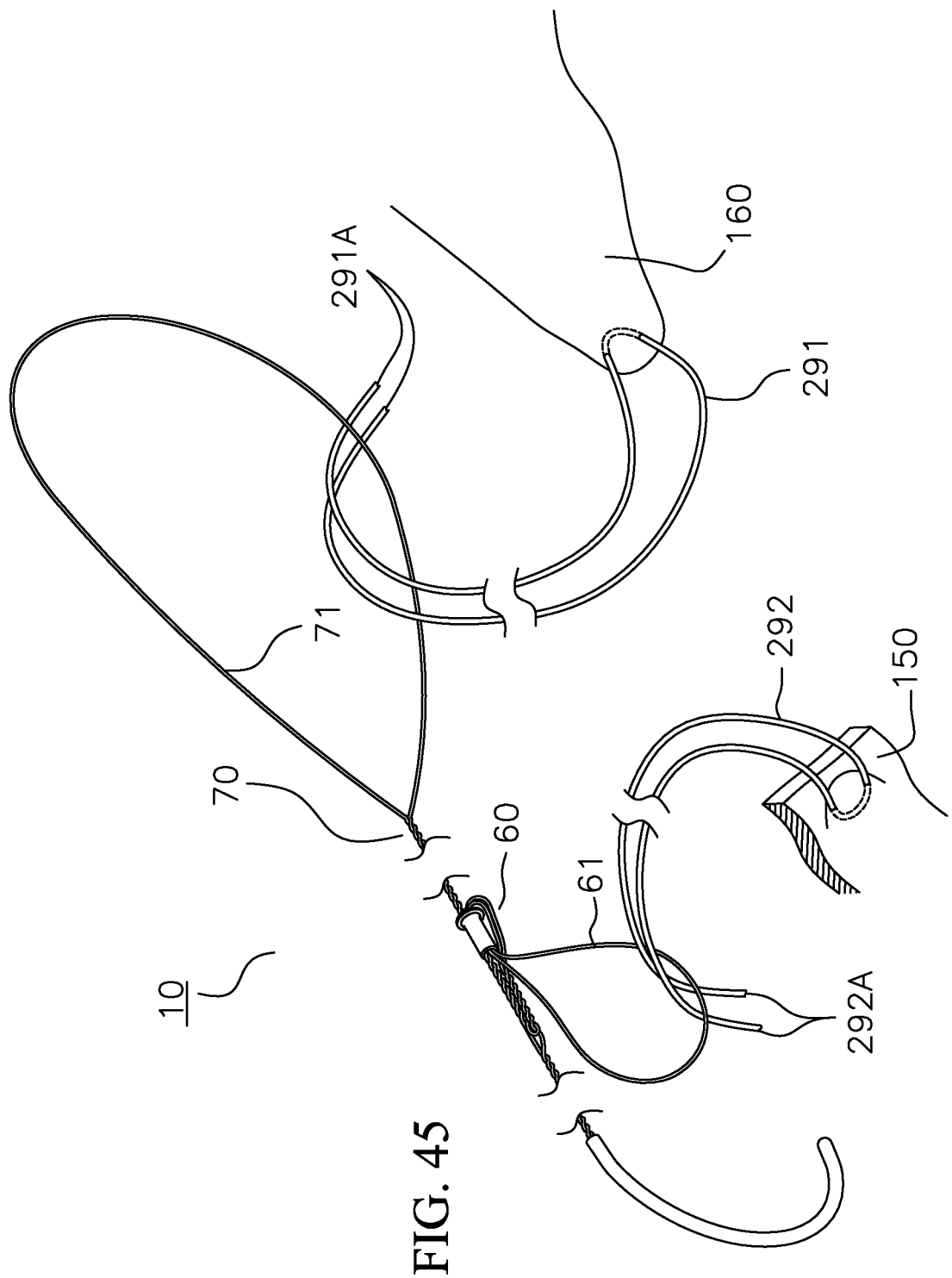
FIG. 45 is a perspective view illustrating the application of two separate emplaced sutures with the apparatus first shown in FIG. 1.
Figure 46:
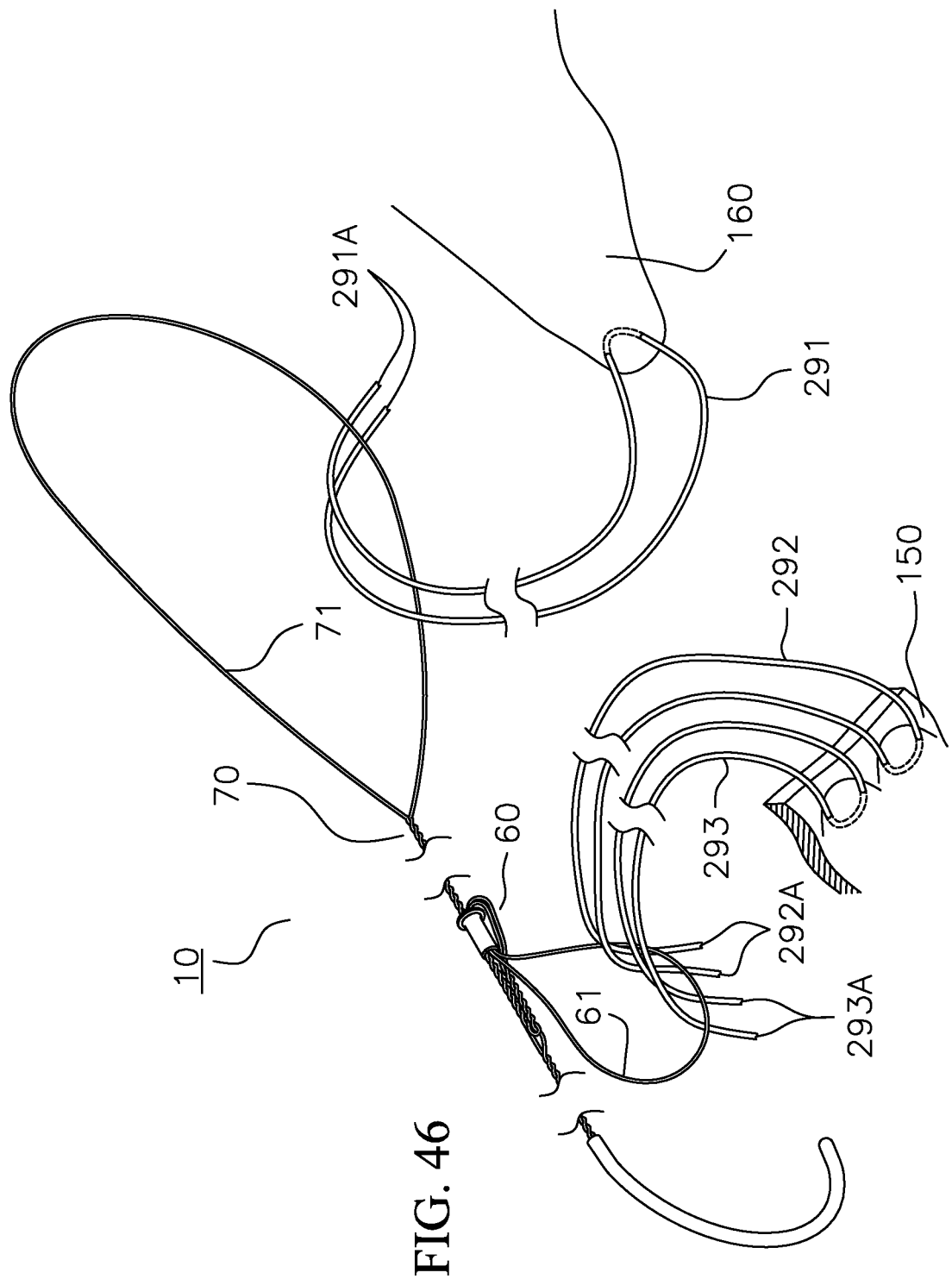
FIG. 46 is a perspective view illustrating the application of three separate emplaced sutures with the apparatus first shown in FIG. 1.

Referring to FIGS. 44 through 46, a variety of therapeutic configurations is detailed in conjunction with the bidirectional snare device 10. FIG. 44 is a perspective view of a bidirectional snare device 10 being loaded with a single suture 290 with a suture tail 290A placed through a papillary muscle 160 and fed through the loop 71 of the long wire snare 70 of the bidirectional snare device 10 and the other suture tail 290B placed through a leaflet 150 and fed through the loop 61 of the short wire snare 60 of the bidirectional snare device 10.

FIG. 45 is a perspective view of a bidirectional snare device 10 being loaded with a suture 291 placed through a papillary muscle 160 and the suture tails 291A fed through the loop 71 of the long wire snare 70 of the bidirectional snare device 10 and a suture 292 placed through a leaflet 150 and the suture tails 292A fed through the loop 61 of the short wire snare 60 of the bidirectional snare device 10.

FIG. 46 is a perspective view of a bidirectional snare device 10 being loaded with a suture 291 placed though a papillary muscle 160 and the suture tails 291A fed through the loop 71 of the long wire snare 70 of the bidirectional snare device 10 and sutures 292 and suture 293 placed through a leaflet 150 and the suture tails 292A and suture tails 293A, respectively, fed through the loop 61 of the short wire snare 60 of the bidirectional snare device 10.

FIGS. 47A through 49B are perspective views illustrating a variety of configurations of coaxial mechanical fasteners 30. FIG. 47A illustrates the use of the single suture 290 forming a loop 290C proximal to the body 83 of the sleeve 80 and a loop 290D distal to the flange 82 of the sleeve 80. Suture tail 290A and suture tail 290B exit the sleeve 80 opposite each other.

FIG. 47B illustrates the routing of the suture 290 with the sleeve 80 removed for clarity.

FIG. 48A illustrates the use of the suture 292 forming a loop 292B proximal to the body 83 of the sleeve 80 and the single suture 291 forming a loop 291B distal to the flange 82 of the sleeve 80. Suture tails 291A and suture tails 292A exit the sleeve 80 opposite each other.

FIG. 48B illustrates the routing of the suture 291 and suture 292 with the sleeve 80 removed for clarity.

FIG. 49A illustrates the use of the suture 292 and suture 293 both forming separate loops 292B and 293B, respectively, proximal to the body 83 of the sleeve 80 along with a suture 291 forming a loop 291B distal to the flange 82 of the sleeve 80. Suture tails 292A and suture tails 293A exit the sleeve 80 together at the flange 82 opposite from suture tails 291A exiting from the body 83.

FIG. 49B illustrates the routing of the suture 291, suture 292, and suture 293 with the sleeve 80 removed for clarity.

FIG. 50 is a perspective view of the deployment device 20 with an attached slotted suture securing reel 330 which is used to maintain coaxial alignment of the papillary suture 324 and leaflet suture 325 with the shaft tube 230 of the deployment device 20 while also aiding in suture management. A yard arm 340 of the slotted suture securing reel 330 is positioned on the shaft tube 230 and secured with a screw 380 through a second bore 343. The yard arm 340 is typically of a machined stainless steel or the like and has the ability to flex slightly about a flexure groove 342. The leaflet suture 325 is placed within a slot 341 and is free to slide coaxial to the shaft tube 230. The papillary suture 324 is placed between compression rings 360, which are customarily made of a rubber material, and secured via a knurled knob 370 that is comprised of a machined metal or molded plastic and whose threaded bore 371 (best shown in FIG. 51) is threaded onto a threaded shaft 381 (also best shown in FIG. 51) of the screw 380, which is also typically stainless steel, and applies compressional force onto reel plates 350, which can be manufactured as machined metal or molded plastic, and subsequently the compression rings 360.

FIG. 51 is an exploded perspective view of the slotted suture securing reel 330 of FIG. 50. The yard arm 340 is attached to the shaft tube 230 of the deployment device 20 by the compressional force applied by the knurled knob 370 whose threaded bore 371 is threaded onto the threaded shaft 381 of the screw 380 and subsequently compresses the reel plates 350 whose bores 351 fit over the threaded shaft 381 of screw 380 and compression rings 360 whose internal diameters 361 also fit over the threaded shaft 381 of screw 380.

While the invention has been described in connection with a number of presently preferred embodiments thereof, those skilled in the art will recognize that a number of modifications and changes may be made therein without departing from the true spirit and scope of the invention which accordingly is intended to be defined solely by the appended claims.

The invention claimed is:

1. A surgical suturing instrument comprising:
   a handle;
   an actuator on the handle;
   an elongated shaft extending distally from the handle along a shaft axis from a proximal end to a distal end, the shaft including one or more fluid apertures disposed between an outer surface of the shaft and an inner surface of the shaft, wherein the inner surface of the shaft at least partially defines an interior portion of the shaft;
   an elongated wedge tip at least partially disposed in the interior portion of the shaft, the wedge tip extending along a wedge tip axis from a proximal end to a distal end, wherein the proximal end of the wedge tip is coupled to the actuator, wherein one or more fluid troughs are each defined by one or more exterior surfaces of the wedge tip, each of the one or more fluid troughs extending along the wedge tip axis from a proximal end to a distal end that is at the distal end of the wedge tip, and wherein when the actuator is in a first position, the distal end of the wedge tip is in an unactuated position and when the actuator is in a second position, the distal end of the wedge tip is in an actuated position;
   a crimper assembly configured to crimp a suture fastener, the crimper assembly disposed adjacent the distal end of the shaft, the crimper assembly comprising:
      a suture fastener receiver configured to receive the suture fastener, the suture fastener receiver extending from a first end to a second end along a receiver axis that is parallel to the shaft axis such that the suture fastener is configured to be inserted into the suture fastener receiver along the receiver axis; and
      a hammer anvil, wherein the distal end of the wedge tip selectively engages a portion of the hammer anvil, the hammer anvil configured to (a) retain the suture fastener when the suture fastener is disposed in the suture fastener receiver and the distal end of the wedge tip is in the unactuated position and (b) crimp the suture fastener when the suture fastener is disposed in the suture fastener receiver and the distal end of the wedge tip is in the actuated position and engages the portion of the hammer anvil; and
   a fluid housing coupled to a portion of the shaft that is proximal to the distal end of the shaft, wherein a communication bore extends through a portion of the fluid housing from a first end of the communication bore to a second end of the communication bore, wherein the second end of the communication bore is disposed adjacent to and in fluid communication with each of the one or more fluid apertures of the shaft,
   wherein when an infusing fluid is introduced through the first end of the communication bore, the infusing fluid flows through the communication bore to the second end of the communication bore, through the one or more fluid apertures of the shaft, through each of the one or more fluid troughs of the wedge tip, and to an infusion port disposed through the suture fastener receiver of the crimper assembly for delivering the infusing fluid to a surgical site.

2. The surgical suturing instrument of claim 1 comprising a suture cutter disposed proximately to the crimper assembly.

3. The surgical suturing instrument of claim 2 in which the suture cutter is coupled to the actuator, such that the cutter is actuated after the crimper assembly is actuated.

4. The surgical suturing instrument of claim 3, in which the crimper assembly and the cutter are actuated by a single squeeze of the actuator.

5. The surgical suturing instrument of claim 3, comprising a projection for positioning a suture for cutting.

6. The surgical suturing instrument of claim 1, comprising a suture holder disposed on the shaft between the handle and the distal end of the shaft for temporarily holding a suture.

7. The surgical suturing instrument of claim 1, further comprising a fluid seal coupled to the wedge tip proximal to the proximal end of each of the one or more fluid troughs, wherein the fluid seal sealingly engages the inner surface of the shaft when the distal end of the wedge tip is in the unactuated position and the actuated position.

8. The surgical suturing instrument of claim 1, wherein the fluid housing is coupled to the portion of the shaft that is at or adjacent to the proximal end of the shaft.

* * * * *